(12) United States Patent
Li et al.

(10) Patent No.: US 8,822,954 B2
(45) Date of Patent: Sep. 2, 2014

(54) PHOSPHOR BASED AUTHENTICATION SYSTEM

(75) Inventors: Yi-Qun Li, Danville, CA (US); Haitao Yang, San Jose, CA (US)

(73) Assignee: Intematix Corporation, Fremont, CA (US)

( * ) Notice: Subject to any disclaimer, the term of this patent is extended or adjusted under 35 U.S.C. 154(b) by 804 days.

(21) Appl. No.: 12/604,268

(22) Filed: Oct. 22, 2009

(65) Prior Publication Data

US 2010/0102250 A1    Apr. 29, 2010

Related U.S. Application Data

(60) Provisional application No. 61/107,928, filed on Oct. 23, 2008.

(51) Int. Cl.
*G01N 21/64* (2006.01)

(52) U.S. Cl.
USPC ............................................. 250/459.1

(58) Field of Classification Search
USPC ............................................. 250/459.1
See application file for complete search history.

(56) References Cited

U.S. PATENT DOCUMENTS

| | | | |
|---|---|---|---|
| 3,290,255 A | 12/1966 | Smith |
| 3,593,055 A | 7/1971 | Geusic et al. |
| 3,670,193 A | 6/1972 | Thorington et al. |
| 3,676,668 A | 7/1972 | Collins et al. |
| 3,691,482 A | 9/1972 | Pinnow et al. |
| 3,709,685 A | 1/1973 | Hercock et al. |
| 3,743,833 A | 7/1973 | Martie et al. |
| 3,763,405 A | 10/1973 | Mitsuhata |
| 3,793,046 A | 2/1974 | Wanmaker et al. |
| 3,819,973 A | 6/1974 | Hosford |

(Continued)

FOREIGN PATENT DOCUMENTS

| CN | 101076835 A | 11/2007 |
|---|---|---|
| EP | 647694 | 4/1995 |

(Continued)

OTHER PUBLICATIONS

International Search Report and Written Opinion dated Dec. 14, 2009 for International Application No. PCT/US2009/061896, 9 pages.

(Continued)

*Primary Examiner* — David Porta
*Assistant Examiner* — Shun Lee
(74) *Attorney, Agent, or Firm* — Vista IP Law Group, LLP

(57) ABSTRACT

A phosphor (photo-luminescent) material based authentication system in which a blend (mixture) of at least two, preferably three or more, phosphor materials are used as a photo-luminescent security marking which is applied to or incorporated within an article/document to be authenticated. Preferably, the phosphor materials are each excitable by "eye safe" excitation radiation comprising visible light of wavelength 380 nm to 780 nm. Moreover, when excited the security marking preferably also emits visible light thereby minimizing any risk of damage to an operator's eye in the event of accidental exposure to the excitation radiation and/or light generated by the photo-luminescent marking. The authenticity of the article/document can be authenticated by verification of the composition of the phosphor by exciting the marking and comparing one or more selected parameters of light emitted by the security marking with corresponding parameters of the characteristic emission spectrum of the authentic phosphor blend.

22 Claims, 9 Drawing Sheets

(56) References Cited

U.S. PATENT DOCUMENTS

| | | |
|---|---|---|
| 3,819,974 A | 6/1974 | Stevenson et al. |
| 3,849,707 A | 11/1974 | Braslau et al. |
| 3,875,456 A | 4/1975 | Kana et al. |
| 3,932,881 A | 1/1976 | Mita et al. |
| 3,937,998 A | 2/1976 | Verstegen et al. |
| 3,972,717 A | 8/1976 | Wiedemann |
| 4,047,075 A | 9/1977 | Schoberl |
| 4,081,764 A | 3/1978 | Christmann et al. |
| 4,104,076 A | 8/1978 | Pons |
| 4,143,394 A | 3/1979 | Schoberl |
| 4,176,294 A | 11/1979 | Thornton, Jr. |
| 4,176,299 A | 11/1979 | Thornton |
| 4,211,955 A | 7/1980 | Ray |
| 4,305,019 A | 12/1981 | Graff et al. |
| 4,315,192 A | 2/1982 | Skwirut et al. |
| 4,443,532 A | 4/1984 | Joy et al. |
| 4,559,470 A | 12/1985 | Murakami et al. |
| 4,573,766 A | 3/1986 | Bournay, Jr. et al. |
| 4,618,555 A | 10/1986 | Suzuki et al. |
| 4,638,214 A | 1/1987 | Beers et al. |
| 4,667,036 A | 5/1987 | Iden et al. |
| 4,678,285 A | 7/1987 | Ohta et al. |
| 4,727,003 A | 2/1988 | Ohseto et al. |
| 4,772,885 A | 9/1988 | Uehara et al. |
| 4,845,223 A | 7/1989 | Seybold et al. |
| 4,859,539 A | 8/1989 | Tomko et al. |
| 4,915,478 A | 4/1990 | Lenko et al. |
| 4,918,497 A | 4/1990 | Edmond |
| 4,946,621 A | 8/1990 | Fouassier et al. |
| 4,992,704 A | 2/1991 | Stinson |
| 5,077,161 A | 12/1991 | Law |
| 5,110,931 A | 5/1992 | Dietz et al. |
| 5,126,214 A | 6/1992 | Tokailin et al. |
| 5,131,916 A | 7/1992 | Eichenauer et al. |
| 5,143,433 A | 9/1992 | Farrell |
| 5,143,438 A | 9/1992 | Giddens et al. |
| 5,166,761 A | 11/1992 | Olson et al. |
| 5,208,462 A | 5/1993 | O'Connor et al. |
| 5,210,051 A | 5/1993 | Carter, Jr. |
| 5,211,467 A | 5/1993 | Seder |
| 5,237,182 A | 8/1993 | Kitagawa et al. |
| 5,264,034 A | 11/1993 | Dietz et al. |
| 5,283,425 A | 2/1994 | Imamura |
| 5,331,140 A | 7/1994 | Stephany |
| 5,369,289 A | 11/1994 | Tamaki et al. |
| 5,405,709 A | 4/1995 | Littman et al. |
| 5,439,971 A | 8/1995 | Hyche |
| 5,518,808 A | 5/1996 | Bruno et al. |
| 5,535,230 A | 7/1996 | Abe |
| 5,557,168 A | 9/1996 | Nakajima et al. |
| 5,563,621 A | 10/1996 | Silsby |
| 5,578,839 A | 11/1996 | Nakamura et al. |
| 5,583,349 A | 12/1996 | Norman et al. |
| 5,585,640 A | 12/1996 | Huston et al. |
| 5,619,356 A | 4/1997 | Kozo et al. |
| 5,660,461 A | 8/1997 | Ignatius et al. |
| 5,677,417 A | 10/1997 | Muellen et al. |
| 5,679,152 A | 10/1997 | Tischler et al. |
| 5,763,901 A | 6/1998 | Komoto et al. |
| 5,766,324 A | 6/1998 | Ikegaya et al. |
| 5,770,887 A | 6/1998 | Tadatomo et al. |
| 5,771,039 A | 6/1998 | Ditzik |
| 5,777,350 A | 7/1998 | Nakamura et al. |
| 5,869,199 A | 2/1999 | Kido |
| 5,959,316 A | 9/1999 | Lowery |
| 5,962,971 A | 10/1999 | Chen |
| 6,137,217 A | 10/2000 | Pappalardo et al. |
| 6,340,824 B1 | 1/2002 | Komoto et al. |
| 6,490,030 B1* | 12/2002 | Gill et al. .......... 356/71 |
| 6,504,301 B1 | 1/2003 | Lowery |
| 6,576,488 B2 | 6/2003 | Collins et al. |
| 6,600,175 B1 | 7/2003 | Baretz et al. |
| 6,642,618 B2 | 11/2003 | Yagi et al. |
| 6,642,652 B2 | 11/2003 | Collins et al. |
| 6,686,074 B2 | 2/2004 | Muth et al. |
| 6,841,092 B2 | 1/2005 | Paeschke et al. |
| 6,869,812 B1 | 3/2005 | Liu |
| 7,030,371 B2 | 4/2006 | Vasic et al. |
| 7,153,015 B2 | 12/2006 | Brukilacchio |
| 7,311,858 B2 | 12/2007 | Wang et al. |
| 7,390,437 B2 | 6/2008 | Dong et al. |
| 7,479,662 B2 | 1/2009 | Soules et al. |
| 7,615,795 B2 | 11/2009 | Baretz et al. |
| 7,943,945 B2 | 5/2011 | Baretz et al. |
| 2003/0032192 A1* | 2/2003 | Haubold et al. ........ 436/56 |
| 2004/0016938 A1 | 1/2004 | Baretz et al. |
| 2006/0049416 A1 | 3/2006 | Baretz et al. |
| 2006/0145123 A1 | 7/2006 | Li et al. |
| 2006/0158090 A1 | 7/2006 | Wang et al. |
| 2006/0219673 A1 | 10/2006 | Varnham |
| 2006/0261309 A1 | 11/2006 | Li et al. |
| 2007/0023715 A1* | 2/2007 | Ross et al. ........... 250/556 |
| 2007/0029526 A1 | 2/2007 | Cheng et al. |
| 2007/0295116 A1 | 12/2007 | Le Mercier et al. |
| 2008/0014463 A1 | 1/2008 | Varadarajan et al. |
| 2008/0111472 A1 | 5/2008 | Liu et al. |
| 2008/0224597 A1 | 9/2008 | Baretz et al. |
| 2008/0224598 A1 | 9/2008 | Baretz et al. |
| 2009/0283721 A1 | 11/2009 | Liu et al. |

FOREIGN PATENT DOCUMENTS

| | | |
|---|---|---|
| GB | 2 017 409 | 10/1979 |
| JP | 60170194 | 9/1985 |
| JP | 01-260707 | 10/1989 |
| JP | 4010665 | 1/1992 |
| JP | 4010666 | 1/1992 |
| JP | 04-289691 | 10/1992 |
| JP | 4-321280 | 11/1992 |
| JP | 6207170 | 7/1994 |
| JP | 6-267301 | 9/1994 |
| JP | 07-099345 | 4/1995 |
| JP | 07-235207 | 9/1995 |
| JP | H07331239 A | 12/1995 |
| JP | H08-7614 | 1/1996 |
| JP | 8-250281 | 9/1996 |
| JP | 2001356689 A | 12/2001 |
| WO | WO 9108508 | 6/1991 |
| WO | 00/60527 A1 | 10/2000 |
| WO | WO 00/60527 | 10/2000 |
| WO | WO2006024530 | 3/2006 |
| WO | WO 2006024530 A1 | 3/2006 |

OTHER PUBLICATIONS

Foreign Office Action dated Feb. 26, 2013 for Chinese Appln. No. 200980141958.

"Fraunhofer-Gesellschaft: Research News Special1997", http://www.fhg.de/press/md-e/md1997/sondert2.hlm,(accessed on Jul. 23, 1998), Jan. 1997, Publisher: Fraunhofer Institute.

Adachi, C. et al., "Blue light-emitting organic electroluminescent devices", "Appl. Phys. Lett.", Feb. 26, 1990, pp. 799-801, vol. 56, No. 9.

Akasaki, Isamu, et al., "Photoluminescence of Mg-doped p-type GaN and electroluminescence of GaN p-n junction LED", "Journal of Luminescence", Jan.-Feb. 1991, pp. 666-670, vol. 48-49 pt. 2.

Amano, H., et al., "UV and blue electroluminescence from Al/GaN:Mg/GaN LED treated with low-energy electron beam irradiation (LEEBI)", "Institute of Physics: Conference Series", 1990, pp. 725-730, vol. 106, No. 10.

Apr. 14, 2010 Office Action in U.S. Appl. No. 11/264,124.

Apr. 15, 2009 Office Action in U.S. Appl. No. 11/264,124, issued by Abu I Kalam.

Armaroli, N. et al., "Supramolecular Photochemistry and Photophysics.", "J. Am. Chem. Soc.", 1994, pp. 5211-5217, vol. 116.

Aug. 21, 2006 Office Action in U.S. Appl. No. 10/623,198, issued by Thao X. Le.

Aug. 24, 2007 Office Action in U.S. Appl. No. 11/264,124, issued by Thao X. Le.

Aug. 26, 2010 Office Action in U.S. Appl. No. 12/131,118.

(56) References Cited

OTHER PUBLICATIONS

Berggren, M., et al., "White light from an electroluminescent diode made from poly[3(4-octylphenyl)-2,2'-bithiophene] and an oxadiazole . . . ", "Journal of Applied Physics", Dec. 1994, pp. 7530-7534, vol. 76, No. 11.
Boonkosum, W. et al., "Novel Flat Panel display made of amorphous SiN:H/SiC:H thin film LED", "Physical Concepts and Materials for Novel Optoelectronic Device Applications II", 1993, pp. 40-51, vol. 1985.
Bradfield, P.L., et al., "Electroluminescence from sulfur impurities in a p-n junction formed in epitaxial silicon", "Appl. Phys. Lett", 07110/1989, pp. 10D-102, vol. 55, No. 2.
Chao, Zhang Jin, et al., "White light emitting glasses", "Journal of Solid State Chemistry", 1991, pp. 17-29, vol. 93.
Comrie, M. , "Full Color LED Added to Lumex's Lineup", "EBN", Jun. 19, 1995, p. 28.
CRC Handbook, 63rd Ed., (1983) p. E-201.
Dec. 16, 2004 Office Action in U.S. Appl. No. 10/623,198, issued by Thao X. Le.
Dictionary Definition of Phosphor, Oxford English Dictionary Online, Mar. 9, 2012 (On Mar. 22, 2012 in U.S. Appl. No. 12/131,119; Request for Full Reference filed).
Feb. 21, 2012 Office Action in U.S. Appl. No. 12/131,118, issued by Abu I Kalam.
Feb. 26, 2008 Office Action in U.S. Appl. No. 11/264,124, issued by Abu I Kalam.
Feb. 4, 2005 Office Action in U.S. Appl. No. 10/623,198, issued by Thao X. Le.
Feb. 7, 2007 Office Action in U.S. Appl. No. 11/264,124, issued by Thao X. Le.
Hamada, Y. et al. , "Blue-Light-Emitting Organic Electroluminescent Devices with Oxadiazole Dimer Dyes as an Emitter", "Jpn. J. Appl. Physics", Jun. 1992, pp. 1812-1816, vol. 31.
Hamakawa, Yoshihiro, et al., "Toward a visible light display by amorphous SiC:H alloy system", "Optoelectronics—Devices and Technologies", Dec. 1989, pp. 281-294, vol. 4, No. 2.
Jan. 29, 2007 Office Action in U.S. Appl. No. 10/623,198, issued by Thao X. Le.
Jan. 30, 2006 Office Action in U.S. Appl. No. 11/264,124, issued by Thao X. Le.
Jan. 7, 2011 Office Action in U.S. Appl. No. 12/131,119, issued by Steven Y. Horikoshi.
Jul. 10, 2008 Office Action in U.S. Appl. No. 11/264,124, issued by Abu I Kalam.
Jul. 14, 2005 Notice of Allowance, Notice of Allowability, and Examiners Statement of Reasons for Allowance in U.S. Appl. No. 10/623,198, issued by Thao X. Le.
Jul. 14, 2011 Office Action in U.S. Appl. No. 12/131,119, issued by Steve Horikoshi.
Jul. 7, 2011 Office Action in U.S. Appl. No. 12/131,118, issued by Abu I Kalam.
Jun. 14, 2006 Office Action in U.S. Appl. No. 11/264,124, issued by Thao X. Le.
Jun. 26, 2007 Office Action in U.S. Appl. No. 10/623,198, issued by Thao X. Le.
Kido, J. et al. , "1,2,4-Triazole Derivative as an Electron Transport Layer in Organic Luminescent Devices", "Jpn. J. Appl. Phys.", Jul. 1, 1993, pp. L917-L920, vol. 32.
Kido, J. et al. , "Bright blue electroluminescence from poly(N-vinylcarbazole)", "Appl. Phys. Letters", Nov. 8, 1993, pp. 2627-2629, vol. 63, No. 19.
Kido, J., et al., "White light-emitting organic electroluminescent devices using the poly(N-vinylcarbazole) emitter layer doped with . . . ", "Appl. Phys. Lett.", Feb. 14, 1994, pp. 815-817, vol. 64, No. 7.
Krames, M., et al., "Status and Future of High-Power Light-Emitting Diodes for Solid-Slate Lighting", "Journal of Display Technology", Jun. 2007, pp. 160-175, vol. 3, No. 2.
Kudryashov, V., et al., "Spectra of Superbright Blue and Green InGaN/AlGaN/GaN Light-Emitting diodes", "Journal of the European Ceramic Society", May 1996, pp. 2033-2037, vol. 17.
Larach, S., et al., "Blue emitting luminescent phosphors: Review and status", "Int'l Workshop on Electroluminescence", 1990, pp. 137-143.
LEDs and Laser Diodes, Electus Distribution, copyright 2001, available at URL:http://www.jaycar.com.au/images_uploaded/ledlaser.Pdf.
Lester, S., et al., "High dislocation densities in high efficiency GaN-based light-emitting diodes", "Appl. Phys. Lett.", Mar. 6, 1995, pp. 1249-1251, vol. 66, No. 10.
Mar. 2, 2009 Office Action in U.S. Appl. No. 10/623,198, issued by Abu I Kalam.
Mar. 22, 2012 Office Action in U.S. Appl. No. 12/131,119, issued by Steven Y. Horikoshi.
Mar. 28, 2006 Office Action in U.S. Appl. No. 10/623,198, issued by Thao X. Le.
Mar. 4, 2011 Notice of Allowance, Notice of Allowability, Examiner's Interview Summary, Examiner's Amendment/Comment and Examiner's Statement of Reason for Allowance in U.S. Appl. No. 11/264,124, issued by Abu I Kalam.
Mar. 7, 2008 Office Action in U.S. Appl. No. 10/623,198, issued by Abu I Kalam.
Maruska, H.P., "Gallium nitride light-emitting diodes (dissertation)", "Dissertation Submitted to Stanford University", Nov. 1973.
Maruska, H.P., et al., "Violet luminescence of Mg-doped GaN", "Appl. Phys. Lett.", Mar. 15, 1973, pp. 303-305, vol. 22, No. 6.
May 4, 2010 Office Action in U.S. Appl. No. 12/131,119.
McGraw-Hill Dictionary of Scientific and Technical Terms, Third Edition, pp. 912, 1446; Copyright 1984.
Mimura, Hidenori, et al., "Visible electroluminescence from uc-SiC/porous Si/c-Si p-n junctions", "Int. J. Optoelectron.", 1994, pp. 211-215, vol. 9, No. 2.
Miura, Noboru, et al., "Several Blue-Emitting Thin-Film Electroluminescent Devices", "Jpn. J. Appl. Phys.", Jan. 15, 1992, pp. L46-L48, vol. 31, No. Part 2, No. 1A IB.
Morkoc, H. et al. , "Large-band-gap SiC, 111-V nitride, and II-VI ZnSe-based semiconductor device technologies ", Aug. 1, 1994, pp. 1363-1398, vol. 76, No. 3.
Mukai, T., et al., "Recent progress of nitride-based light emitting devices", "Phys. Stat. Sol.", Sep. 2003, pp. 52-57, vol. 200, No. 1.
Nakamura, S., et al., "High-power InGaN single-quantum-well-structure blue and violet light-emitting diodes", "Appl. Phys. Lett.", Sep. 25, 1995, pp. 1868-1870, vol. 67, No. 13.
Nakamura, S., et al., "The Blue Laser Diode: GaN Based Light Emitters and Lasers", Mar. 21, 1997, p. 239, Publisher: Springer-Verlag.
Nakamura, S., et al., "The Blue Laser Diode: The Complete Story, 2nd Revised and Enlarged Edition", Oct. 2000, pp. 237-240, Publisher: Springer-Verlag.
Nov. 30, 2010 Office Action in U.S. Appl. No. 12/131,118.
Oct. 20, 2008 Office Action in U.S. Appl. No. 10/623,198, issued by Abu I Kalam.
Pavan, P., et al., "Explanation of Current Crowding Phenomena Induced by Impact Ionization in Advanced Si Bipolar Transistors by Means of . . . ", "Microelectronic Engineering", 1992, pp. 699-702, vol. 19.
Pei, Q, et al., "Polymer Light-Emitting Electrochemical Cells", "Science", Aug. 25, 1995, pp. 1086-1088, vol. 269, No. 5227.
Reexam Advisory Action dated Sep. 28, 2012 for U.S. Appl. No. 90/010,940.
Reexam Final Office Action dated May 24, 2012 for U.S. Appl. No. 90/010,940.
Reexam Final Office Action dated Nov. 7, 2011 for U.S. Appl. No. 90/010,940.
Reexam Non-Final Office Action dated Jan. 26, 2012 for U.S. Appl. No. 90/010,940.
Reexam Non-Final Office Action dated Mar. 3, 2011 for U.S. Appl. No. 90/010,940.
Reexam Non-Final Office Action dated Sep. 20, 2010 for U.S. Appl. No. 90/010,940.
Saleh and Teich, Fundamentals of Photonics, New York: John Wiley & Sons, 1991, pp. 592-594.

(56) References Cited

OTHER PUBLICATIONS

Sato, Yuichi, et al., "Full-color fluorescent display devices using a near-UV light-emitting diode", "Japanese Journal of Applied Physics", Jul. 1996, pp. L838-L839, vol. 35, No. ?A.

Sep. 17, 2009 Notice of Allowance, Notice of Allowability, Examiners Amendmeni/Comment, and Examiners Statement of Reasons for Allowance in U.S. Appl. No. 10/623,198, issued by Abu I Kalam.

Sep. 29, 2009 Office Action in U.S. Appl. No. 11/264,124, issued by Abu I Kalam.

Tanaka, Shosaku, et al., "Bright white-light electroluminescence based on nonradiative energy transfer in Ce-and Eu-doped SrS thin films", "Applied Physics Letters", Nov. 23, 1987, pp. 1661-1663, vol. 51, No. 21.

Tanaka, Shosaku, et al., "White Light Emitting Thin-Film Electroluminescent Devices with SrS:Ce,Cl/ZnS:Mn Double Phosphor Layers", "Jpn. J. Appl. Phys.", Mar. 20, 1986, pp. L225-L227, vol. 25, No. 3.

The Penguin Dictionary of Electronics, 3rd edition, pp. 315,437-438, 509-510, copyright 1979, 1988, and 1998.

Ura, M. , "Recent trends of development of silicon monocarbide blue-light emission diodes", "Kinzoku ", 1989, pp. 11-15, vol. 59, No. 9.

Yamaguchi, Y. et al., "High-Brightness SiC Blue LEDs and Their Application to Full Color LED Lamps", "Optoelectronics-Devices and Technologies", Jun. 1992, pp. 57-67, vol. 7, No. 1.

Yoshimi, Masashi, et al., "Amorphous carbon basis blue light electroluminescent device", "Optoelectronics—Devices and Technologies", Jun. 1992, pp. 69-81, vol. 7, No. 1.

Zanoni, E., et al., "Impact ionization, recombination, and visible light emission in ALGaAs/GaAs high electron mobility transistors", "J. Appl. Phys.", 1991, pp. 529-531, vol. 70, No. 1.

Zanoni, E., et al., "Measurements of Avalanche Effects and Light Emission in Advanced Si and SiGe Bipolar Transistors", "Microelectronic Engineering", 1991, pp. 23-26, vol. 15.

Zdanowski, Marek, "Pulse operating up-converting phosphor LED", "Electron Technol. ", 1978, pp. 49-61, vol. 11, No. 3.

Zhiming, Chen, et al., "Amorphous thin film white-LED and its light-emitting mechanism", "Conference Record of the 1991 International Display Research Conference", Oct. 1991, pp. 122-125.

Foreign Office Action dated Nov. 12, 2013 for Japanese Appln. No. 2011-533379.

Chinese Office Action dated Dec. 18, 2013 for Chinese Patent Appln. No. 200980141958.X.

\* cited by examiner

PHOSPHOR BASED AUTHENTICATION SYSTEM

CLAIM OF PRIORITY

This application claims priority to U.S. Provisional Patent Application No. 61/107,928 filed Oct. 23, 2008, by Yi-Qun Li et al., titled "Phosphor Based Authentication System." U.S. Provisional Patent Application No. 61/107,928 is incorporated herein by reference in its entirety.

BACKGROUND OF THE INVENTION

1. Field of the Invention

The present invention relates to a phosphor (photo-luminescent) material based authentication system and, more particularly, to a method of authenticating a photo-luminescent security marking, an apparatus for authenticating a photo-luminescent security marking and a photo-luminescent security marking.

2. Description of the Related Art

Authentication is the act of establishing or confirming something as being genuine, that is, claims made about the thing are true. Authenticating an article or document usually involves confirming its provenance using one or more authentication factors. Articles or documents will often include one or more security markings or security devices in order to authenticate the article/document. Examples of security markings/devices include: watermarks in documents, magnetic print on personal checks, micro-printing on banknotes, antibodies in oil and gas, molecular recognition agents in spirits and liquors, thermal transfer inks and color shifting pigments on packaging, holograms on credit cards, photo-luminescent security markings, bar codes, electronic tagging devices, invisible markers on pharmaceuticals capsules etc.

A study sponsored by the World Economic Forum (WEF) estimates the rate of counterfeiting goods such as pharmaceuticals, tobacco, luxury goods, electronics, clothing, and other items is between 7 and 9% of global trade and totals more than $700 billion per annum. The World Health Organization (WHO) and FDA (US Food and Drug Administration) estimate that anything between 5 and 8% of pharmaceutical and related products are counterfeit. In addition to jeopardizing people's health, counterfeiting results in a loss of revenue of the order of $30 million a year.

Due to continuing improvements in color printing and image scanning technologies the counterfeiting of documents, such as for example, bank notes, identification papers, passports, drivers' licenses, admission tickets is increasing. Additionally, counterfeiting of credit, debit and security cards is increasing due to the widespread availability of computers and card readers. Brand protection has become a huge strategic issue due to globalization of trade, organized crime and the high profits with often low penalties associated with counterfeiting.

To combat counterfeiting and safeguard a brand, a variety of security technologies have been developed including RFID (Radio Frequency Identification), holography, stable isotopic markers, molecular recognition markers, thermo-chromic materials, color shift inks, tags with visible and invisible fluorescent dyes, and phosphor material based markings.

Security markings that utilize a phosphor material offer a number of potential authentication factors including excitation wavelength, emission spectra with unique signatures covering ultra violet (UV) to near infrared (NIR), peak intensity, peak wavelength, decay time or interval, rise and fall of particular peaks in the spectra. To verify the authenticity of an article or document it is known to provide a phosphor security marking on the article/document. The authenticity of the article/document is verified by irradiating the article with high energy radiation from a source such as a UV lamp and measuring the intensity of UV light reflected from the object and the amount of fluorescent light generated by the phosphor security marking. If the optical characteristics (reflection and emission) are within prescribed limits, then the article is verified as being genuine.

Phosphor (photo-luminescent) materials can be characterized into two categories i) down-converting and ii) up-converting. In the case of down-converting photo-luminescent materials, the material is excited with high energy photons such as UV or high ionizing radiations such as X-rays or γ-rays and emit light in the visible or NIR spectral regions. Conversely up-converting, or anti-Stokes, photo-luminescent materials absorb two or more low energy photons such as NIR, particularly 980 nm radiation, and emit a single high energy photon of shorter wavelength (e.g. visible light) by a process of summing IR photons.

Most UV excitable down-converting phosphors, hereinafter termed UV phosphors, can be excited by 254 nm or 365 nm lines from a low pressure mercury vapor lamp. By analyzing the emission (photo luminescence) spectra, the identity of the phosphor can be determined. UV phosphors were extensively used in security markers during the 1980s and 1990s. A drawback of UV phosphors is that most of them fluoresce strongly on paper based substrates and this can reduce the effectiveness of the fluorescent marking. A further problem with UV phosphors is that the UV excitation radiation is harmful to the human eye. From a safety perspective phosphors that can be excited by an excitation radiation of wavelength within the visible part of the electromagnetic spectrum, that is 380 to 700 nm, are considered to be ideal.

The up-conversion process relies on one absorber $Yb^{3+}$ (ytterbium) and typically one or more of three different emitters in blue $Tm^{3+}$ (thulium), green $Er^{3+}$ (erbium) or red $Yb^{3+}$ regions. Absorption of a first infrared photon promotes a rare earth ion into a relatively long-lived first excited state. If a subsequent infrared photon encounters this excited ion it may, depending on the absorption probability, be absorbed, thereby promoting the ion into a second higher excited state. Transition of the ion from the second state to the ground state results in the emission of a photon of higher energy (i.e. of shorter wavelength). Since up-converting phosphor materials rely on the absorbance of $Yb^{3+}$ each of them can be excited by a 980 nm (IR) laser diode. An example of an up-converting phosphor is a $Eu^{3+}$, $Yb^{3+}$ activated yttrium oxysulfide $Y_2O_2S$: Er,Yb. Other examples of IR (980 nm) excitable phosphors are $Yb^{3+}$, $Tm^{3+}$ activated gadolinium oxysulfide as are described in U.S. Pat. No. 6,686,074 and U.S. Pat. No. 6,841,092.

A problem with up-converting phosphors is that due to their relatively low efficiency they need to be excited by high intensity IR radiation generated by a laser and such radiation is harmful to the human eye. To reduce the likelihood of eye damage WO 2000/60527 teaches exciting an up-converting phosphor material using an NIR laser that is operated in a pulsed mode of operation such that the pulses have a peak power sufficient to induce a detectable emission in the phosphor material and the pulse repetition frequency and duration are selected such that the mean power of the laser emission is low enough not to produce eye damage.

Inks containing UV phosphors are readily available in the security industry at a relatively low cost. However, due to the widespread use of such inks counterfeiters have become knowledgeable about various inks and their use. Moreover, counterfeiters are able to reproduce or procure the same ink with UV phosphors that matches the characteristics of the ink with phosphor from the product sample, and apply the same on the counterfeit products. To overcome this problem, ink with up-converting phosphors that are excitable by light in the IR part of the spectrum ranging from 800 nm to 1600 nm have been developed. U.S. Pat. No. 5,766,324 describes an IR security ink that comprises an IR phosphor combined with a black colorant which does not absorb light in the IR wavelength range.

U.S. Pat. No. 7,030,371 discloses a method of measuring the luminescence characteristic of a luminescent security marking in which the luminescence emission is measured during specific time intervals either during or after exposure to the excitation radiation. The intensity value measured during one time interval is subtracted from the intensity value measured during the other time interval with the result of the subtraction being representative of light emitted from the luminescent security marking. The duration of one time interval is shorter than 25% of the exposure time to the excitation radiation.

U.S. Pat. No. 5,331,140 discloses a bar code reading system for reading a fluorescent bar code. The bar code is irradiated with radiation that is sine wave or square wave modulated at two frequencies that are not harmonically related and detecting radiation emitted by the bar code at frequencies corresponding to the sum and difference of the two modulation frequencies.

A need exists for an inexpensive authentication system that offers a high level of security and which can be verified using a portable authentication device.

SUMMARY OF THE INVENTION

Embodiments of the invention are directed to a phosphor based authentication system that utilizes a photo-luminescent security marking that comprises a blend of two or more phosphor materials that are, preferably, each excitable by "eye safe" excitation radiation comprising visible light of wavelength 380 nm to 780 nm. Preferably, when excited the security marking also emits visible light thereby substantially eliminating any risk of damage to an operator's eye in the event of accidental exposure to the excitation radiation and/or light generated by the photo-luminescent marking.

According to the invention there is provided a method of authenticating a photo-luminescent security marking in which an authentic security marking comprises a blend of at least two phosphor materials that are excitable by excitation radiation of a selected wavelength that is within a wavelength range 380 to 780 nm and which when excited has a known emission characteristic, the method comprising: a) irradiating the marking with excitation radiation of the selected wavelength, b) measuring at least one selected parameter of light emitted by the marking, and c) comparing the at least one measured parameter with a corresponding parameter of the known emission characteristic and verifying the authenticity of the marking if the parameters are within prescribed limits.

In one arrangement, the marking comprises at least one phosphor material which is only excitable by excitation radiation of wavelength within a first wavelength range and at least one phosphor material which is excitable by excitation radiation of wavelength within a second different wavelength range which overlaps and includes the first wavelength range, the method comprising: a) irradiating the marking with excitation radiation of wavelength within the first wavelength range and measuring at least one selected parameter of light emitted by the marking, b) irradiating the marking with excitation radiation of wavelength that is within the overlapping region of the first and second wavelength ranges and measuring at least one selected parameter of light emitted by the marking, c) irradiating the marking with excitation radiation of wavelength within a part of the second wavelength range that does not overlap the first wavelength range and measuring at least one selected parameter of light emitted by the marking, and d) comparing the at least one measured parameters measured with corresponding parameters of the known emission characteristic and verifying the authenticity of the marking if the parameters are within prescribed limits.

Conveniently, the selected parameter comprises the intensity of emitted light within one or more selected wavelength regions, typically a wavelength region including an expected emission peak resulting from one of the phosphor materials. In one arrangement the authenticity of the marking is verified by comparing the relative intensities (i.e. ratio) of emitted light within the selected regions with the corresponding ratios for the known emission characteristic. Alternatively and/or in addition the selected parameter can comprise the intensity and/or wavelength of an emission peak, the rate of rise and/or fall of an emission peak, the ratio of emission peak intensities and/or wavelengths, intensity and/or of an emission trough, the ratio of emission trough intensities and/or wavelengths, wavelength and/or intensity of a point of inflection, the ratio of point of inflection intensities and/or wavelengths, the number of emission peaks, troughs and/or points of inflection, the shape of an emission peak or trough or the general shape and/or form of the emission spectrum.

The concept of using a photo-luminescent marking that comprises a blend or mixture of two phosphor materials in which one phosphor material is excitable by excitation radiation of a first wavelength range and a second phosphor material is excitable by excitation radiation of a second different wavelength range which overlaps and includes the first wavelength range is considered inventive in its own right. Thus according to a second aspect of the invention there is provided a method of authenticating a photo-luminescent security marking in which an authentic security marking comprises a blend of at least two phosphor materials in which at least one phosphor material is only excitable by excitation radiation of wavelength within a first wavelength range and at least one phosphor material is excitable by excitation radiation of wavelength within a second different wavelength range which overlaps and includes the first wavelength range, the method comprising: irradiating the marking with excitation radiation of wavelength within the first wavelength range and measuring at least one selected parameter of light emitted by the marking, irradiating the marking with excitation radiation of wavelength that is within the overlapping region of the first and second wavelength ranges and measuring at least one selected parameter of light emitted by the marking, irradiating the marking with excitation radiation of wavelength within a part of the second wavelength range that does not overlap the first wavelength range and measuring at least one selected parameter of light emitted by the marking, and comparing the measured at least one selected parameters with corresponding parameters of the known emission characteristic and if the parameters are within prescribed limits verifying the authenticity of the marking.

According to a third aspect of the invention there is provided an apparatus for authenticating a photo-luminescent security marking in which an authentic security marking comprises a blend of at least two phosphor materials that are excitable by excitation radiation of a selected wavelength that is within a wavelength range 380 to 780 nm and which when excited has a known emission characteristic, said apparatus comprising: at least one excitation source operable to emit and irradiate the marking with excitation radiation of the selected wavelength; a detector operable to measure at least one selected parameter of light emitted by the marking; and processing means for comparing the at least one measured parameter with a corresponding parameter of the known emission characteristic and if the they are within prescribed limits verifying the authenticity of the marking.

In one implementation the apparatus further comprises wavelength separating means for dividing the light emitted by the photo-luminescent security marking into selected wavelength regions and the detector is operable to measure the intensity for each selected wavelength regions. The wavelength separating means can comprise one or more optical filters such as gel filters, optical fiber gratings, a grating or a prism.

According to a another aspect of the invention there is provided an apparatus for authenticating a photo-luminescent security marking of a type comprising at least one phosphor material which is only excitable by excitation radiation of wavelength within a first wavelength range and at least one phosphor material which is excitable by excitation radiation of wavelength within a second different wavelength range which overlaps and includes the first wavelength range, the apparatus comprising: a first independently operable excitation source operable to emit and irradiate the marking with excitation radiation of wavelength within the first wavelength range; a second independently operable excitation source operable to emit and irradiate the marking with excitation radiation of wavelength within the second wavelength range; a detector operable to measure at least one selected parameter of light emitted by the photo-luminescent security marking; and processing means for comparing the at least one selected parameter with a corresponding parameter of the known emission characteristic and verifying the authenticity of the marking if the parameters are within prescribed limits; wherein the apparatus is operable a) to irradiate the marking radiation of the first wavelength range and to measure the at least one selected parameter of light emitted by the marking, b) to irradiate the marking with excitation radiation of the first and second wavelength ranges and to measure the at least one selected parameter of light emitted by the marking, c) to irradiate the marking radiation within the part of the second wavelength range that does not overlap the first wavelength range and to measure the at least one selected parameter of light emitted by the marking and d) to compare values of the at least one selected parameter with corresponding parameters of the known emission characteristic and verifying the authenticity of the marking if the parameters are within prescribed limits.

As with the method of the invention the apparatus of the invention verifies (authenticates) the authenticity of the photo-luminescent security marking on the basis of one or more selected parameters that can include: the intensity of a selected wavelength region, ratio of intensities of selected wavelength regions, intensity and/or wavelength of an emission peak, rate of rise and/or fall of an emission peak, ratio of emission peak intensities and/or wavelengths, intensity and/or wavelength of an emission trough, ratio of emission trough intensities and/or wavelengths, wavelength and/or intensity of a point of inflection, ratio of point of inflection intensities and/or wavelengths, number of emission peaks, troughs and/or points of inflection or shape of emission peak.

Preferably, when excited the security marking emits visible light thereby minimizing the risk of damage to an operator's eye in the event of accidental exposure to the excitation radiation and/or light generated by photo-luminescent marking.

Since the phosphor materials preferably comprise down-converting materials the at least one excitation source is preferably operable to generate excitation radiation of wavelength range 400 to 450 nm. Typically, the at least one excitation source comprises one or more light emitting diodes.

According to further aspect of the invention a photo-luminescent security marking comprises a blend of at least two, preferably at least three, phosphor materials in which each phosphor material is excitable by excitation radiation of a selected wavelength that is within wavelength range 380 to 780 nm. In one arrangement the phosphor materials have the same host lattice structure. An advantage of a blend of phosphor materials having the same host matrix is that such a composition makes it more difficult to analyze and determine the exact phosphor blend to counterfeit the photo-luminescent security marking.

In one embodiment each phosphor material is excitable by excitation radiation of the same selected wavelength range. In an another embodiment at least one phosphor material is only excitable by excitation radiation of a first wavelength range and at least one phosphor material is excitable by excitation radiation of a second different wavelength range which overlaps and includes the first wavelength range.

Preferably, when the marking comprises a blend of at least three phosphor materials, at least one phosphor material is excitable by excitation radiation of a first wavelength range, at least one phosphor material is excitable by excitation radiation of a second wavelength range which overlaps and includes the first wavelength range, and at least one phosphor material is excitable by excitation radiation of a third wavelength range which overlaps and includes the first and second wavelength ranges.

Preferably, when excited the security marking emits visible light thereby minimizing the risk of damage to an operator's eye in the event of accidental exposure to the excitation radiation and/or light generated by photo-luminescent marking. Accordingly, the phosphor materials preferably comprise down-converting materials that are excitable by excitation radiation of wavelength 400 to 450 nm.

To enable thorough mixing of the phosphor materials each phosphor material preferably has an average particle size of five microns or less, preferably two microns or less or one micron or less.

The photo-luminescent security marking can comprise a blend of inorganic or organic phosphor materials including aluminate, silicate, nitride, sulfate, oxy-nitride, oxy-sulfate and garnet based phosphor materials. The marking can comprise a blend of down-converting and up-converting phosphor materials that are excitable by a respective excitation source.

The blend of phosphor materials can be incorporated with a binder material, such as an ink, and the mixture then applied to the surface of an article or document by for example ink jet printing, letterpress, intaglio, screen printing or other printing deposition methods. Alternatively, the blend of phosphor materials can be incorporated in a polymer material, such as for example a polycarbonate, acrylic or silicone material, which is then fabricated into sheets or fibers (threads/filaments) which can then be incorporated into a document or other article such as luxury goods or brand clothing. It is also contemplated to laminate the blend of phosphor materials between sheets of material, such as a polymer or paper, in which at least one sheet is transmissive to the excitation radiation and light emitted by the phosphor materials. The laminated sheet can then be applied to, for example, a credit/bank/store card or a part of the card composed of laminated sheet. Alternatively, when the phosphor materials are laminated between paper sheets, the marking can comprise a form of photo-luminescent "water mark" or be applied to the document in the form of a label. In yet another arrangement the phosphor materials are applied to a surface of a metal foil, wire or strip and the foil/wire/strip applied to a surface of the article or incorporated within a document such as a banknote.

To further enhance the security of the photo-luminescent marking it is further contemplated that the phosphor materials be incorporated as part of a bar code or other encoding scheme. In one arrangement lines (bars) of the bar code comprise different phosphor blends and the sequence of lines of different phosphor materials can be used as a further form of coding.

According to a yet further aspect of the invention there is provided a photo-luminescent security marking comprising a blend of at least two phosphor materials in which at least one phosphor material is only excitable by excitation radiation of a first wavelength range and at least one phosphor material is excitable by excitation radiation of a second wavelength range which overlaps and includes the first wavelength range.

BRIEF DESCRIPTION OF THE DRAWINGS

In order that the present invention is better understood embodiments of the invention will now be described, by way of example only, with reference to the accompanying drawings in which.

DETAILED DESCRIPTION OF THE INVENTION

Embodiments of the invention are directed to a phosphor (photo-luminescent) material based authentication system in which a blend (mixture) of at least two, preferably three or more, phosphor materials are used as a photo-luminescent security marking which is applied to or incorporated within an article/document to be authenticated. Preferably, the phosphor materials are each excitable by "eye safe" excitation radiation comprising visible light of wavelength 380 nm to 780 nm. Moreover, when excited the security marking preferably also emits visible light thereby substantially eliminating any risk of damage to an operator's eye in the event of accidental exposure to the excitation radiation and/or light generated by the photo-luminescent marking. Typically the photo-luminescent security marking has a characteristic emission spectrum having two or more peaks and article/document can be verified (authenticated) by verification of the composition of the phosphor by comparing one or more selected parameters of light emitted by the security marking with corresponding parameters of the characteristic emission spectrum of the authentic phosphor blend.

In this specification a phosphor material that is excitable by excitation radiation within a selected wavelength range means that the phosphor is capable of being excited by excitation radiation of a wavelength within the selected wavelength range such that it emits light of sufficient intensity as to be measurable by a photodetector such as a photodiode. It does not require that the wavelength range of the excitation radiation be that for a maximum spectral efficiency.

Figure 1:
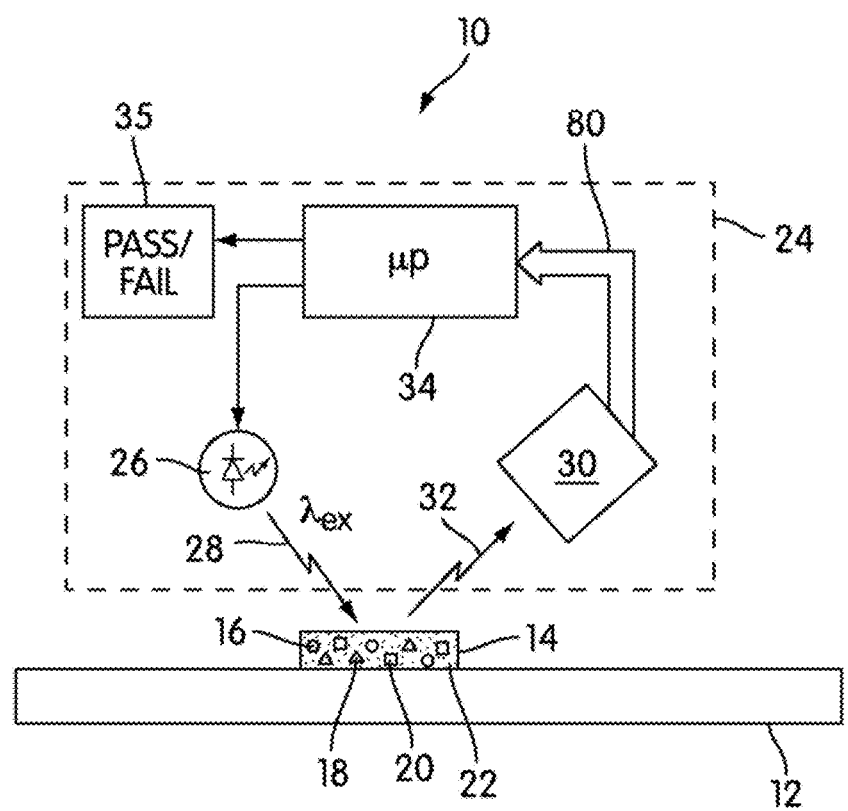
FIG. 1 is a schematic diagram of an authentication system in accordance with the invention.

FIG. 1 is a schematic diagram of an authentication system 10 in accordance with the invention for verifying the authenticity of an article 12. The article 12 which can, for example, comprise a document such as a banknote, passport, identity document, admission ticket (e.g. a lottery, concert ticket etc) or card such as security, credit or identity card, has a photo-luminescent security marking 14 on a surface thereof. The photo-luminescent security marking 14 comprises a blend of three phosphor materials 16, 18, 20 which are incorporated in a binder material 22, such as an ink, and the mixture is then applied to the surface of the object 12 by for example ink jet printing, letterpress, intaglio, screen printing or other printing or deposition methods. The blend of phosphor materials can be incorporated with a binder material, such as an ink, and the mixture then applied to the surface of an article or document by for example ink jet printing, letterpress, intaglio, screen printing or other printing deposition methods. Alternatively, the blend of phosphor materials can be incorporated in a polymer material, such as for example a polycarbonate, acrylic or silicone material, which is then fabricated into sheets or fibers (threads/filaments) which can then be incorporated into a document or other article such as luxury goods or brand clothing. It is also contemplated to laminate the blend of phosphor materials between sheets of material, such as a polymer or paper, in which at least one sheet is transmissive to the excitation radiation and light emitted by the phosphor materials. The laminated sheet can then be applied to, for example, a credit/bank/store card or a part of the card composed of laminated sheet. Alternatively, when the phosphor materials are laminated between paper sheets, the marking can comprise a form of photo-luminescent "water mark" or be applied to the document in the form of a label. In yet another arrangement the phosphor materials are applied to a surface of a metal foil, wire or strip and the foil/wire/strip applied to a surface of the article or incorporated within a document such as a banknote.

In FIG. 1 the phosphor materials are respectively indicated by circular 16, triangular 18 and square 20 symbols. Each phosphor material preferably comprises a down-converting phosphor that has the same host matrix which when excited by excitation radiation of wavelength $\lambda_{ex}$ give rise to a respective emission peak "a", "b", "c" at a respective wavelength $\lambda_a$, $\lambda_b$, $\lambda_c$ in the emission characteristic of the phosphor material blend. Excitation radiation $\lambda_{ex}$ that is not absorbed by the phosphor materials within the photo-luminescent security marking will be reflected and will give rise to an emission peak "d" at a wavelength $\lambda_{ex}$.

The authenticity of the article 12 is verified using a portable, preferably hand held, authentication device 24 (indicated by a dashed line box in FIG. 1) by verifying the authenticity of the photo-luminescent security marking 14 through one or more selected parameters of its characteristic emission spectrum. The authentication device 24 comprises an excitation source 26 which is operable to irradiate the photo-luminescent security marking 14 with excitation radiation 28 of wavelength $\lambda_{ex}$ and a detector arrangement 30 for measuring radiation 32 generated by photo-luminescence of the photo-luminescent security marking 14. The excitation source 26 and detector arrangement 30 are operated under control of a controller 34 which can comprise a microprocessor or dedicated circuitry such as a FPGA (Field Programmable Gate Array). The excitation source 26 preferably comprises one or more light emitting diodes (LEDs) which generates excitation radiation 28 that is "eye safe" and within the visible part of the electromagnetic spectrum (i.e. 380 to 780 nm) to minimize damage to an operator's eye in the event that they are exposed to the excitation radiation 28. The choice of excitation wavelength $\lambda_{ex}$ will depend on the composition of the phosphor blend and whether the phosphor materials are down-converting or up-converting. Preferably, when excited the security marking emits visible light thereby substantially eliminating any risk of damage to an operator's eye in the event of accidental exposure to the excitation radiation and/or light generated by the photo-luminescent marking. Due to their higher efficiency, the phosphor materials preferably comprise down-converting materials and are excited by excitation radiation of comprising blue light in a wavelength range 400 to 450 nm. When up-converting phosphors are used the excitation radiation can comprise red to NIR (Near Infra Red) light within a wavelength range $\lambda_{ex}$=650 to 1000 nm.

Figure 2:
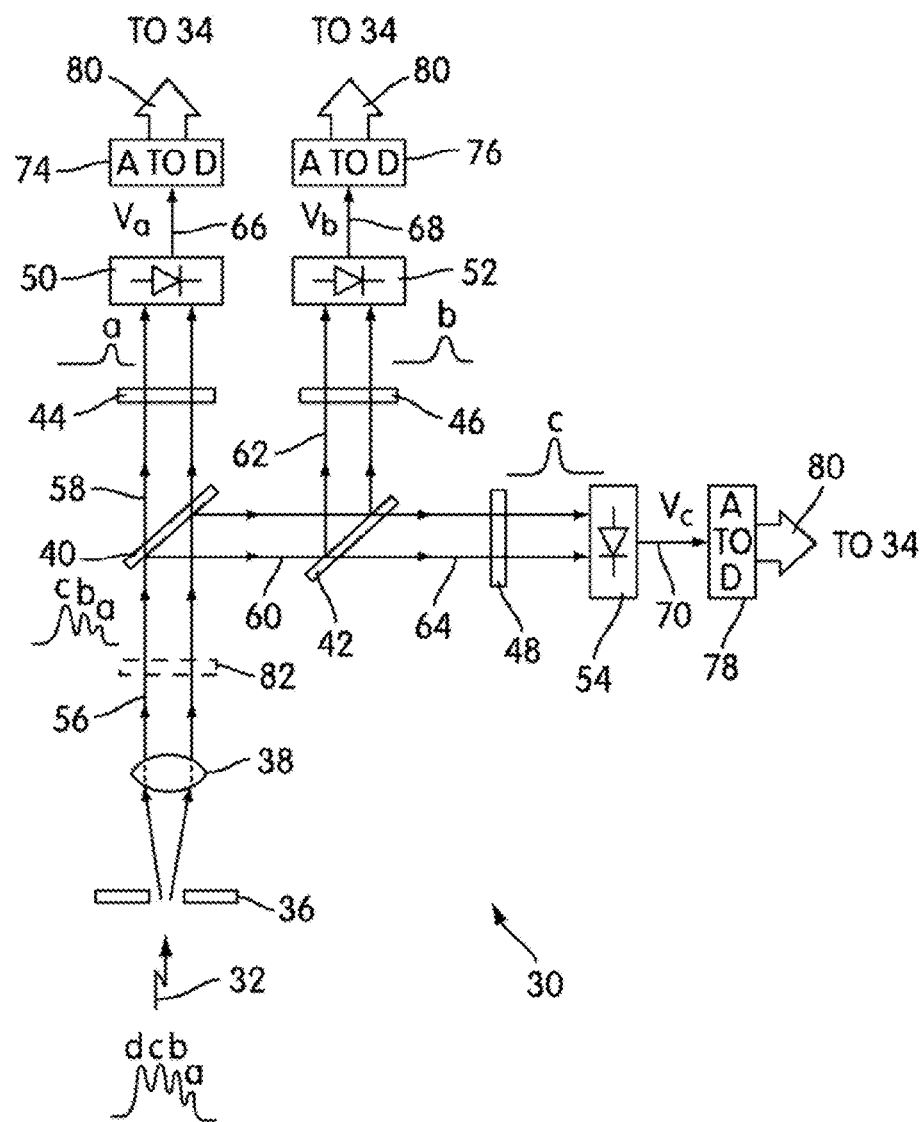
FIG. 2 is a schematic representation of a detector arrangement in accordance with a first embodiment of the invention.

FIG. 2 is a schematic representation of a detector arrangement 30 in accordance with a first embodiment of the invention and comprises a receiving aperture 36, a collimating lens 38, first and second optical splitters 40, 42, first, second and third optical band pass (BP) filters 44, 46, 48, first, second and third photo-detectors 50, 52, 54 and first, second and third analogue to digital (A to D) converters 74, 76, 78. Light 32 emitted/reflected by the article 12 is received by the receiving aperture 36 and is collimated by the collimating lens 38 into a substantially parallel beam 56 which is incident on the first beam splitter 40. The light 32 emitted by the article 12 will comprise a combination of excitation radiation 28 reflected by the article/marking and light generated by photo-luminescence of the phosphor materials within the photo-luminescent security marking 14. The optical splitter 40 can comprise a partially reflecting mirror such as, for example, a half-silvered mirror which is configured such that the beam 56 strikes the mirror at an angle of 45° and is divided into two beams 58, 60 of substantially equal intensity. One beam 58 is transmitted by the optical splitter 40 and the other beam 60 is reflected by the splitter. The light 58 transmitted by the optical splitter 40 is filtered by the first optical band pass (BP) filter 44 and the filtered light transmitted by the filter is detected by the first photo-detector 50. The first optical band pass filter 44 has an optical transmission pass band that corresponds to the expected first emission peak "a" such that in operation the first photo-detector 50 will measure the intensity of light corresponding to the first emission peak "a", that is light centered at the wavelength $\lambda_a$. The first photo-detector thus produces an electrical signal ($V_a$) 66 whose magnitude (voltage) is related to the intensity of light at the wavelength $\lambda_a$.

Each of the optical band pass filters 44, 46, 48 can comprise a gel filter that comprises various inorganic or organic compounds incorporated in a glass or plastics material, typically a polycarbonate or acrylic. Alternatively, the filters 44, 46, 48 can comprise dichroic filters in which multiple optical layers are deposited on a transparent substrate, typically a glass substrate. Whilst dichroic filters offer a superior optical performance in terms of a very precise pass band, they are more expensive to fabricate and it is preferred for economy to use gel filters whenever appropriate.

The light 60 reflected by the first optical splitter 40 is further divided by the second optical splitter 42 into two beams 62, 64 of substantially equal intensity, one of which is reflected 62 and one which is transmitted 64. Light 62 reflected by the second splitter 42 is filtered by the second optical band pass filter 46 and the filtered light transmitted by the filter is detected by the second-photo detector 52. The second optical band pass filter has an optical pass band characteristic that corresponds to the second emission peak "b" such that in operation the second photo detector 52 will measure the intensity of light corresponding to the second emission peak "b", that is light of wavelength centered at the wavelength $\lambda_b$. The second photo-detector 52 thus produces an electrical signal ($V_b$) 68 whose magnitude (voltage) is related to the intensity of light at the wavelength $\lambda_b$.

The light 64 transmitted by the second optical splitter 42 is filtered by the third optical band pass filter 48 and the filtered light transmitted by the filter is detected by the third photo-detector 54. The third optical band pass filter 48 has an optical pass band characteristic that corresponds to the third emission peak "c" such that in operation the third photo-detector 54 will measure the intensity of light corresponding to the third emission peak "c", that is light centered at the wavelength $\lambda_c$. The third photo-detector thus produces an electrical signal ($V_c$) 70 whose magnitude (voltage) is related to the intensity of light at the wavelength $\lambda_c$.

The electrical signals 66, 68, 70 generated by the photo-detectors 50, 52, 54, which are voltages $V_a$, $V_b$, $V_c$ that are respectively related to the intensity of light centered at the wavelengths $\lambda_a$, $\lambda_b$, $\lambda_c$, are converted into numeric values representative of the measured intensity by a respective analogue to digital (A to D) converter 74, 76 78. The numeric values are read by the processor 34 over a data bus 80.

In operation the processor 34 compares the ratios of the three numeric values (e.g. voltages $V_a:V_b$, $V_b:V_c$, $V_a:V_c$, $V_a:V_b:V_c$) with the corresponding ratios expected for the authentic phosphor blend and if they correspond within preselected limits (margins) the photo-luminescent security marking 14, and hence article 12, are deemed to be authenticated. The authentication device 24 indicates to a user that the marking is authenticated by means of an indicator 35 (See FIG. 1) such as an audible indicator (a beep), a visual indicator such as a particular color light (e.g. green) or by another physical indicator such as a low frequency vibration which can be felt by an operator. In the event that the measured ratios are not within prescribed limits, the device preferably generates a corresponding negative indicator 35 (e.g. a red light).

Optionally, the detector arrangement 30 can further comprise an optical filter 82 for blocking the excitation radiation $\lambda_{ex}$. As indicated in FIG. 2 the filter 82 can be provided between the collimating lens 38 and the first optical splitter 40 or provided as a part of the receiving aperture 36. When the photo-luminescent marking comprises a blend of down-converting phosphor materials the filter 82 has an optical characteristic that will transmit light of wavelengths longer than $\lambda_{ex}$ substantially unattenuated whilst substantially blocking light of wavelength equal to or shorter than $\lambda_{ex}$.

It will be appreciated that since the measured light 32 is divided (split) on the basis of intensity (power) the light intensities measured by the photo-detectors 50, 52, 54 will not be absolute intensity values. For example, as a result of the first optical splitter 40, the intensity value measured by the photo-detector 50 will be approximately half the value for the light received by the receiving aperture 36 whilst the intensity values measured by the photo-detectors 52, 54 will be approximately a quarter of their actual value due to the effect of the second optical splitter 42. As a result the values can be scaled by the processor 34 before calculating the relative ratios of peak intensities or the authentication device 24 can be calibrated using a reference security marking composed of an authentic blend of phosphors. Moreover, due to the optical power dividing arrangement the band pass of the first optical band pass filter 44 is selected to correspond to the peak with the lowest expected intensity.

In other embodiments the detector arrangement 30 can further include an additional optical splitter, optical band pass filter and photo-detector for measuring the intensity of light corresponding to the excitation wavelength $\lambda_{ex}$. With such an arrangement the device can verify the authenticity of the emission spectra on the basis of the magnitude of the emission peaks "a", "b", "c" that have been normalized to the magnitude of the excitation radiation peak.

Figure 3:
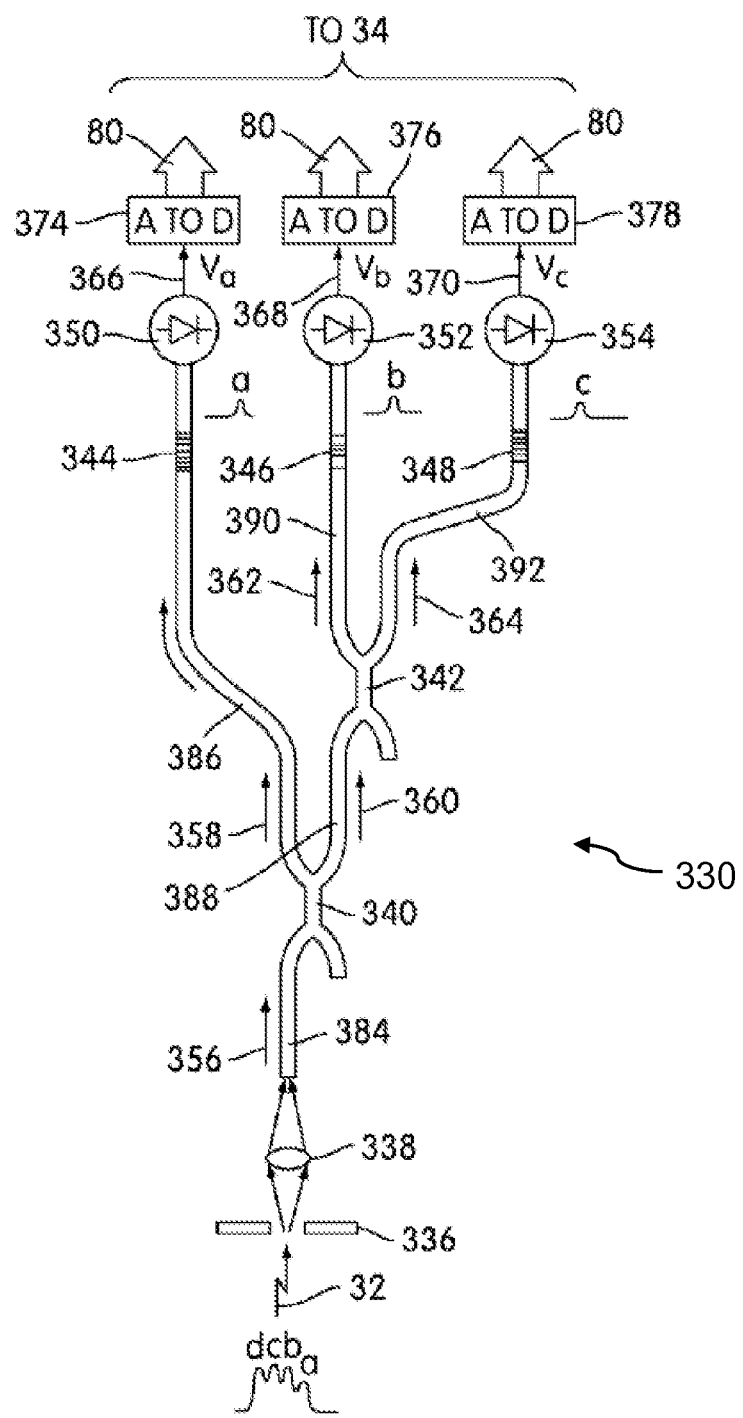
FIG. 3 is a schematic representation of an optical fiber based detector arrangement in accordance with a second embodiment of the invention.

As well as detector arrangements 30 that use free space optics such as that illustrated in FIG. 2 it is also contemplated in other embodiments to use optical arrangements in which the light is guided within an optical medium such as an optical fiber or a solid state waveguide. An advantage of waveguided arrangements is that they enable fabrication of a more compact detector arrangement that is less susceptible to vibration or shock. An example of such a detector arrangement 330 is shown in FIG. 3. Like reference numerals preceded by the first figure number corresponding to a given embodiment are used to denote like parts. For example the photo-detectors 50, 52, 54 of FIG. 2 are respectively denoted 350, 352, 354 in FIG. 3.

FIG. 3 is a schematic representation of an optical fiber based detector arrangement 330 that is functionally equivalent to the detector arrangement 30 of FIG. 2. Light 32 received by the receiving aperture 336 is coupled, by a collimating lens 338, into a first optical fiber 384. The light 356 is guided by the first optical fiber 384 to a first optical splitter 340 where it is divided equally between second and third optical fibers 386 and 388 respectively. The optical splitter 340 typically comprises a fused fiber splitter/coupler. Light 358 within the second optical fiber 386 is filtered by a first optical band pass filter 344 and light transmitted by the filter detected by the first photo-detector 350.

Preferably the optical band pass filters 344, 346, 348 comprise an optical fiber Bragg grating. As is known a fiber Bragg grating comprises a periodic perturbation of the effective refractive index in the core of an optical fiber. Typically, the perturbation is approximately periodic over a certain length (e.g. a few millimeters or centimeters) and the period is of the order of hundreds of nanometers. Fiber Bragg gratings are created by "inscribing" or "writing" the periodic variation of refractive index into the core of an optical fiber using an intense ultraviolet (UV) source such as a UV laser (e.g. KrF or ArF excimer laser) which induces structural changes and thus a permanent modification of the refractive index. An advantage of using optical fiber gratings is that it possible to fabricate a band pass filter with a very narrow pass band (of the order of 1 nm) enabling the detector arrangement to discriminate between closely wavelength spaced peaks.

The first fiber Bragg grating 344 has an optical transmission pass band characteristic (determined by the grating structure) that allows the substantially unattenuated transmission of light with a wavelength corresponding to the expected first emission peak "a" whilst reflecting light of other wavelengths (that is light including the emission peaks "b", "c" and "d"). Consequently, in operation the first photo-detector 350 will measure the intensity of light corresponding to the first emission peak "a" that is light of wavelength centered at the wavelength $\lambda_a$. The first photo-detector 350 thus produces an electrical signal ($V_a$) 366 whose magnitude (voltage) is related to the intensity of light at the wavelength $\lambda_a$.

Light 360 within the third optical fiber 388 is further divided by a second optical splitter 342 equally into fourth and fifth optical fibers 390 and 392 respectively. Light 362 within the fourth optical fiber 390 is filtered by the second optical band pass filter (fiber Bragg grating) 346 and the filtered light transmitted by the filter is detected by the second-photo detector 352. The second optical band pass filter 346 has an optical pass band characteristic (determined by the grating structure) that corresponds to the second emission peak "b" such that in operation the second photo detector 352 will measure the intensity of light corresponding to the second emission peak "b", that is light with a wavelength centered at the wavelength $\lambda_b$. The second photo-detector 352 thus produces an electrical signal ($V_b$) 368 whose magnitude (voltage) is related to the intensity of light at the wavelength $\lambda_b$.

Light 364 within the fifth optical fiber 392 is filtered by the third optical band pass filter 348 and the filtered light transmitted by the filter is detected by the third photo-detector 354. The third optical band pass filter (fiber Bragg grating) 348 has an optical pass band characteristic that corresponds to the third emission peak "c" such that in operation the third photo-detector 354 will measure the intensity of light corresponding to the third emission peak "c", that is light with a wavelength centered at the wavelength $\lambda_c$. The third photo-detector 354 thus produces an electrical signal ($V_c$) 370 whose magnitude (voltage) is related to the intensity of light at the wavelength $\lambda_c$.

The electrical signals 366, 368, 370 generated by the photo-detectors 350, 252, 354 which comprise voltages $V_a$, $V_b$, $V_c$ which are respectively related to the intensity of light at wavelengths $\lambda_a$, $\lambda_b$, $\lambda_c$, are converted into numeric values representative of the measured intensity by a respective analogue to digital (A to D) converter 374, 376 378. The numeric values are read by the processor 34 over the data bus 80.

In operation the processor 34 compares the ratios of the three numeric values (e.g. voltages $V_a:V_b$, $V_b:V_c$, $V_a:V_c$, $V_a:V_b:V_c$) with the ratios expected for the authentic phosphor blend and if they correspond within pre-selected limits (margins) the photo-luminescent security marking 14, and hence article 12, are deemed to be authenticated.

Figure 4:
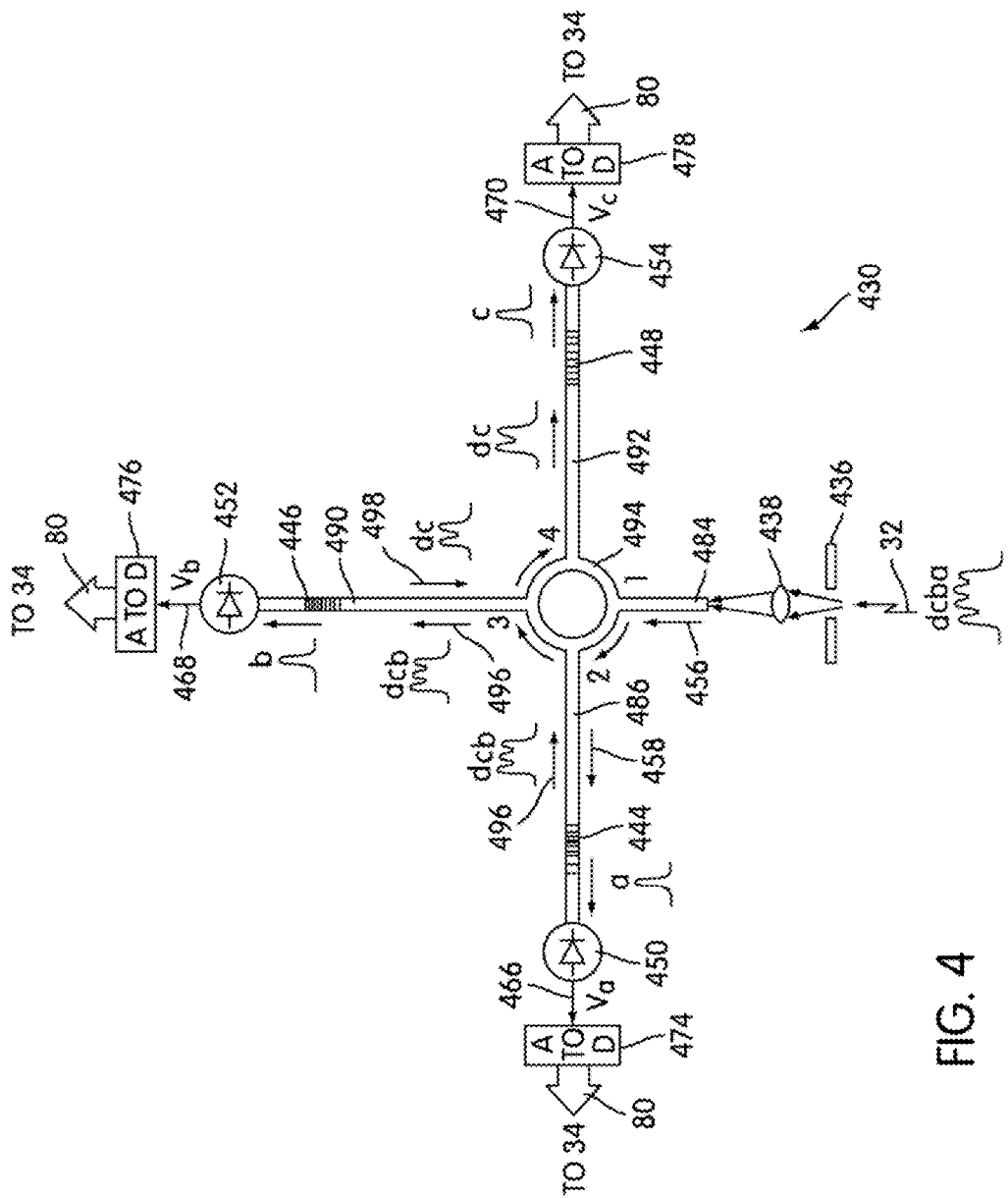
FIG. 4 is a schematic representation of an optical fiber based detector arrangement in accordance with a third embodiment of the invention.

In addition to detector arrangements in which the detected light is divided (split) on the basis of intensity (power) it is also contemplated in other embodiments to divide the measured light on the basis of wavelength range. FIG. 4 is a schematic representation of an optical fiber based detector arrangement 430 in which an optical circulator 494 and fiber Bragg grating filters 444, 446, 448 are used to divide the received light 32 on the basis of wavelength range rather than intensity. Like reference numerals preceded by the figure number are used to denote like parts. For example the photo-detectors 350, 352, 354 of FIG. 3 are respectively denoted 450, 452, 454 in FIG. 4.

Light 32 received by the receiving aperture 436 is coupled, by the collimating lens 438, into the first optical fiber 484. The light 456 is guided by the first optical fiber 484 to a first port 1 of a four port optical circular 494. As is known an optical circulator is a multiport optical fiber component that allows light to travel in only one direction e.g. from port 1 to port 2, then from port 2 to port 3 and so forth. As a result if light emitted from port 2 is reflected back to the circulator, it is directed not back to port 1, but on to port 3. An advantage of an optical circulator is that it has high isolation of the input and reflected optical powers and a very low insertion loss.

The light 458 exits the second port 2 of the optical circulator 494 and travels along the second optical fiber 486 to the first fiber Bragg grating 444. The first fiber Bragg grating 444 has an optical transmission pass band characteristic (determined by the grating structure) that allows the substantially unattenuated transmission of light corresponding to the expected first emission peak "a" whilst reflecting light 496 of other wavelengths (that is light including the emission peaks "b", "c" and "d"). Consequently, in operation the first photo-detector 450 will measure the intensity of light corresponding to the first emission peak "a" that is light with a wavelength centered at the wavelength $\lambda_a$. The first photo-detector 450 thus produces an electrical signal ($V_a$) 466 whose magnitude (voltage) is related to the intensity of light at the wavelength $\lambda_a$.

Light 496 reflected by the first fiber Bragg grating 444 travels back along the first fiber 486 to the second port 2 of the optical circulator 494 and exits the third port 3 of the optical circulator into a fourth optical fiber 490. The light 496 travels along the fourth optical fiber 490 to the second fiber Bragg grating 446. The second fiber Bragg grating 446 has an optical transmission pass band characteristic (determined by the grating structure) that allows the substantially unattenuated transmission of light corresponding to the expected second emission peak "b" whilst reflecting light 498 of other wavelengths (that is light including the emission peaks "c" and "d"). Consequently, in operation the second photo-detector 452 will measure the intensity of light corresponding to the second emission peak "b", that is light with a wavelength centered at the wavelength $\lambda_b$. The second photo-detector 452 thus produces an electrical signal ($V_b$) 468 whose magnitude (voltage) is related to the intensity of light at the wavelength $\lambda_b$.

Light 498 reflected by the second fiber Bragg grating 446 travels back along the fourth optical fiber 490 to the third port 3 of the optical circulator 494 and exits the fourth port 4 of the optical circulator into a fifth optical fiber 492. The light 498 travels along the fifth optical fiber 492 to the third fiber Bragg grating 448. The third fiber Bragg grating 448 has an optical transmission pass band characteristic (determined by the grating structure) that allows the substantially unattenuated transmission of light corresponding to the expected third emission peak "c" whilst reflecting light of other wavelengths (that is light including the emission peak "d"). Consequently, in operation the third photo-detector 454 will measure the intensity of light corresponding to the third emission peak "c" that is light with a wavelength centered at the wavelength $\lambda_c$. The third photo-detector 454 thus produces an electrical signal ($V_c$) 470 whose magnitude (voltage) is related to the intensity of light at the wavelength $\lambda_c$.

The electrical signals 466, 468, 470 generated by the photo-detectors 450, 452, 454, which comprise voltages $V_a$, $V_b$, $V_c$ which are respectively related to the intensity of light at wavelengths $\lambda_a$, $\lambda_b$, $\lambda_c$, are converted into numeric values representative of the measured intensity by a respective analogue to digital (A to D) converter 474, 476 478. The numeric values are read by the processor 34 over a data bus 80.

In operation the processor 34 compares the ratios of the three numeric values (e.g. voltages voltages $V_a$:$V_b$, $V_b$:$V_c$, $V_a$:$V_c$, $V_a$:$V_b$:$V_c$) with the corresponding ratios expected for the authentic phosphor blend and if they correspond within pre-selected limits (margins) the photo-luminescent security marking 14, and hence object 12, are deemed to be authenticated.

It is further contemplated in other detector arrangements to divide the measured light on the basis of wavelength range using other optical components such as bifringent optical splitters.

In each of the detector arrangements described (i.e. those of FIGS. 2, 3 and 4) the authenticity of the photo-luminescent security marking 14 is verified by comparing the ratios and/or normalized magnitudes of the measured emission peaks with those expected for an authentic phosphor blend to verify that they are within pre-selected margins. Whilst such detector arrangements are relatively simple and inexpensive to implement it will be appreciated that the wavelengths ($\lambda_a$, $\lambda_b$, $\lambda_c$) at which the detector arrangement measures light intensity are fixed by the optical characteristics of the band pass filters. As a result such detector arrangements are only suitable for verifying a photo-luminescent security marking with a single phosphor blend. In other embodiments it is contemplated that the detector arrangement comprises a spectrometer arrangement that is capable of measuring the emission spectrum (intensity versus wavelength) of light 32 emitted by the photo-luminescent marker. As will be described in such a detector arrangement the processor 34 can compare other selected parameters of the emitted spectrum with corresponding parameters expected from the authentic phosphor blend to verify the photo-luminescent security marking. Moreover, it will be appreciated that such a detector arrangement can, depending upon its resolution, be used to verify the authenticity of photo-luminescent security markings composed of almost any phosphor blends.

Figure 5:
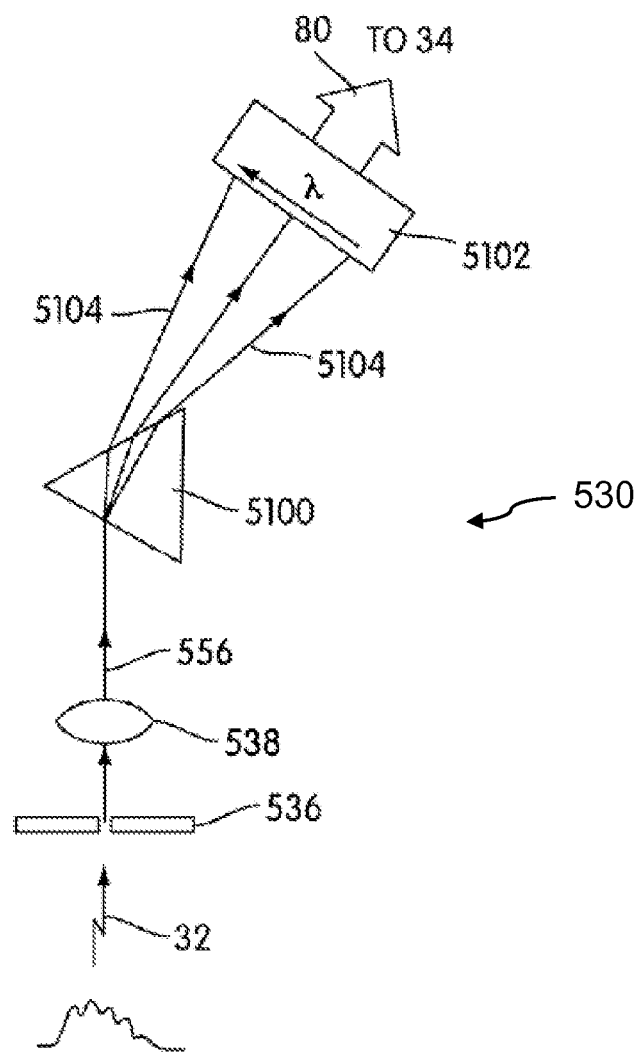
FIG. 5 is a schematic representation of a spectrometer detector arrangement in accordance with a fourth embodiment of the invention.

FIG. 5 is a schematic representation of a spectrometer detector arrangement 530 that uses a prism 5100 to separate wavelength components of the measured light 32. The detector arrangement comprises a receiving aperture 536, typically in the form of a slot (slit), a convex cylindrical lens 538, a prism 5100 and an image sensor 5102. Light 32 emitted by the object 12 is received by the receiving aperture 536 and is collimated by the lens which light 556 is incident on a face of the prism 5100. As is known the prism resolves light into spectral components 5104 dependent on the wavelength of light and these components are detected by the image sensor 5100. The image sensor 5100, which can comprise a charge coupled device (CCD) or complementary metal oxide semiconductor (CMOS) device, measures the intensity of light over a wavelength range which typically corresponds to the visible part of the spectrum. The emission spectrum measured by the image sensor 5100 is passed to the processor 34 over the data bus 80 which then analyzes it and compares selected parameters of the spectrum with corresponding parameters of a standard spectrum to authenticate an object. It will be appreciated that in other arrangements the measured light can be spatially resolved into spectral components using an optical grating or an array waveguide grating (AWG). Additionally, scanning spectrometer arrangements can be used in which the prism or grating is moved such as to scan the light over the sensor. In such an arrangement the sensor can then comprise a simple photodetector.

Figure 6:
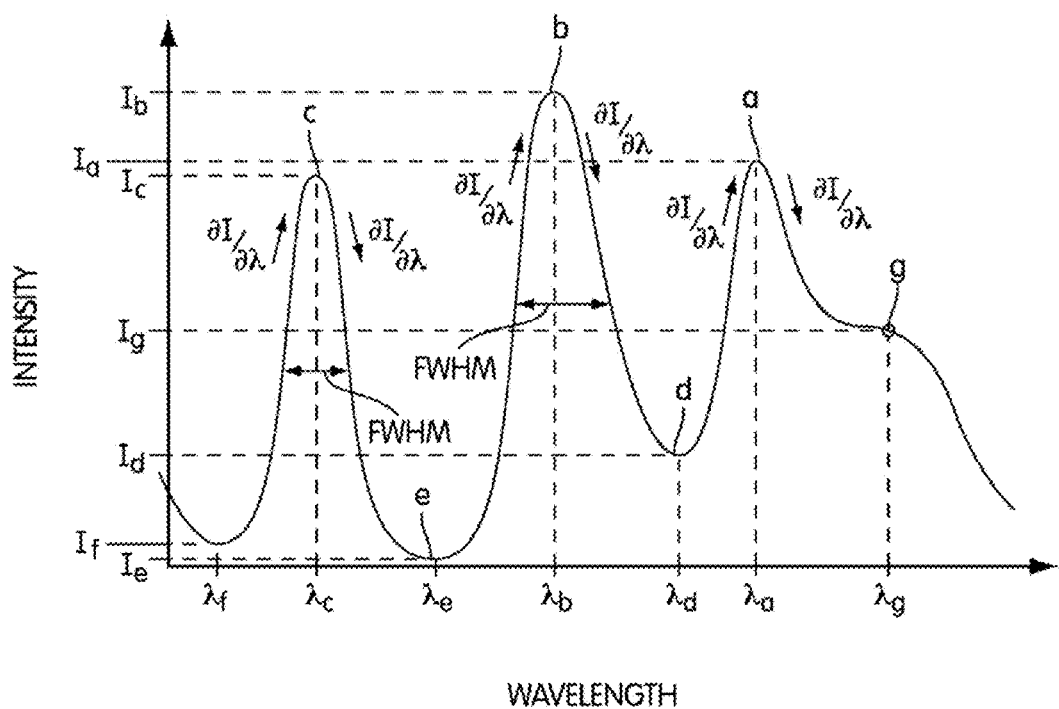
FIG. 6 is a schematic diagram of an emission spectrum indicating parameters used in authenticating the phosphor blend.

Although the ratio of emission peaks is a preferred authenticating parameter other parameters can be used to verify the authenticity of the light emitted by the photo-luminescent marking. Examples of such parameters are illustrated in FIG. 6. The spectrum in FIG. 6 has three peaks "a", "b", "c" at wavelengths ($\lambda_a$, $\lambda_b$, $\lambda_c$) and peak intensities ($I_a$, $I_b$, $I_c$), three troughs "d", "e", "f" at wavelengths ($\lambda_d$, $\lambda_e$, $\lambda_f$) and trough intensities ($I_d$, $I_e$, $I_f$) and one point of inflection "g" at wavelength ($\lambda_g$) and of intensity ($I_g$). The selected parameters can include but are not limited to:

the actual wavelength ($\lambda_a$, $\lambda_b$, $\lambda_c$) and/or intensity ($I_a$, $I_b$, $I_c$) of emission peaks, the actual wavelength ($\lambda_d$, $\lambda_e$, $\lambda_f$) and/or intensity ($I_d$, $I_e$, $I_f$) of emission troughs, the wavelength ($\lambda_g$) and/or intensity ($I_g$) corresponding to points of inflection in the emission spectrum, the rate of rise of emission peaks ($\partial I/\partial \lambda$), the rate of fall of emission peaks ($\partial I/\partial \lambda$), ratio of emission peak intensities (e.g. $I_a:I_b:I_c$, $I_a:I_b$, $I_b:I_c$, $I_a:I_c$), ratio of emission peak wavelengths (e.g. $\lambda_a:\lambda_b:\lambda_c$, $\lambda_a:\lambda_b$, $\lambda_b:\lambda_c$, $\lambda_a:\lambda_c$), ratio of emission peak intensity to emission trough intensity (e.g. $I_a:I_d$, $I_b:I_d$, $I_b:I_e$, $I_c:I_e$, $I_c:I_f$, $I_a:I_e$, $I_a:I_f$, $I_b:I_f$), ratio of emission peak wavelength to emission trough wavelength (e.g. $\lambda_a:\lambda_d$, $\lambda_b:\lambda_d$, $\lambda_b:\lambda_e$, $\lambda_c:\lambda_e$, $\lambda_c:\lambda_f$, $\lambda_a:\lambda_e$, $\lambda_a:\lambda_f$, $\lambda_b:\lambda_f$), peak line width (i.e. full width at half-maximum FWHM), ratio of peak line widths and rate of decay of phosphor photo-luminescence when the excitation source is switched off (not shown in FIG. 6).

As described a photo-luminescent security marking in accordance with the invention comprises a blend of at least two, preferably at least three, phosphor materials such that the blend produces an identifiable emission spectrum when excited by excitation radiation that is "eye safe". Preferably, the different phosphor materials have the same host matrix with differing activators and/or co-activators or differing concentrations. An advantage of a blend of phosphor materials having the same host matrix is that such a composition makes it more difficult to analyze and reverse engineer the phosphor blend to counterfeit the photo-luminescent security marking.

It is preferable that the constituent phosphor materials have a small particle size to ensure better miscibility between the various materials. Preferably, the phosphor blends of the invention consist of phosphor particles whose average particle size (diameter) is smaller than 5 microns (μm), preferably smaller than 2 μm and optionally smaller than 1 μm.

Figure 7A:
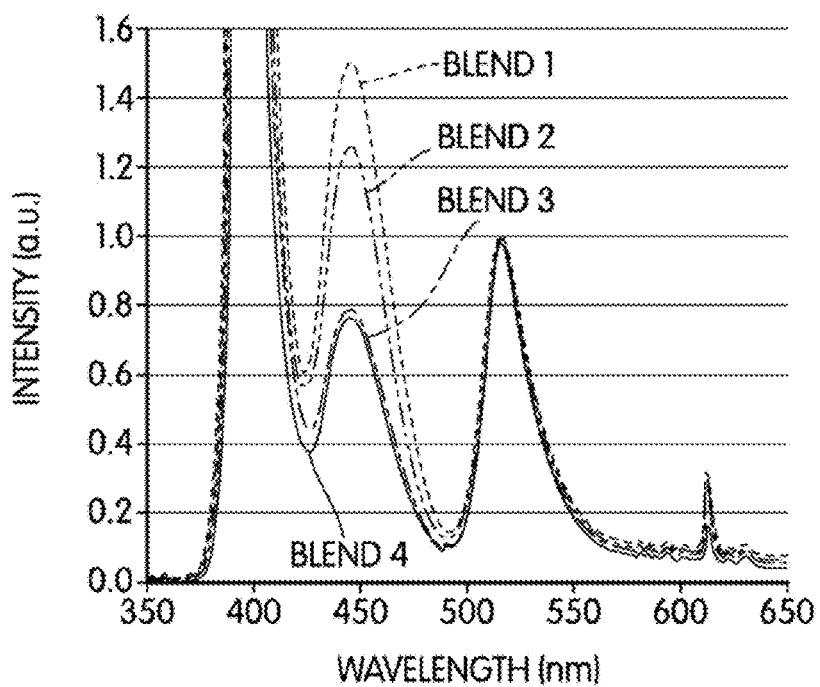
FIG. 7(a) shows normalized emission spectra (intensity versus wavelength) for three phosphor material photo-luminescent security markings of different blends and FIG. 7(b) shows the longer wavelength part of the spectra of FIG. 7(a)
Figure 7B:
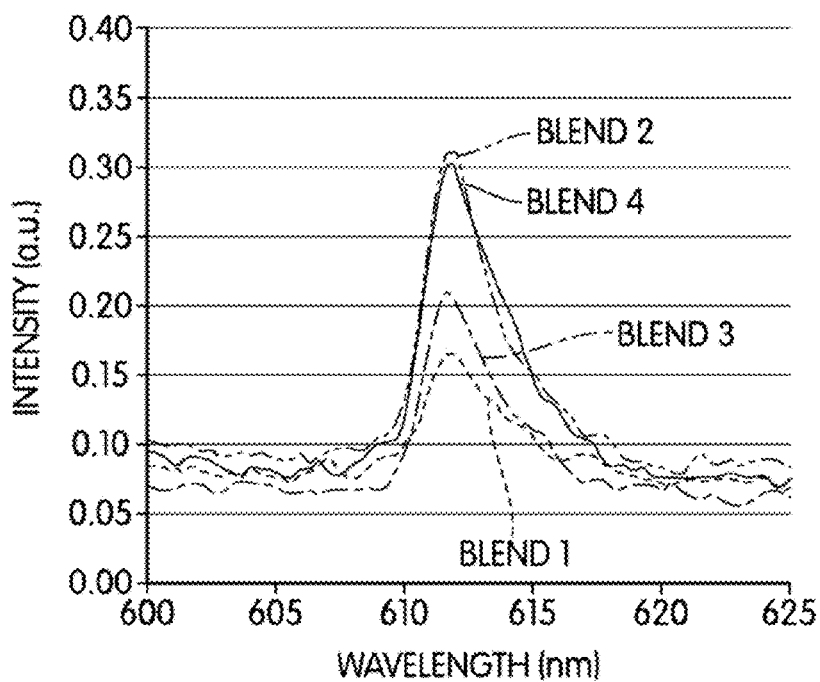

FIGS. 7(a) and 7(b) show normalized emission spectra for four different weight ratio blends of three phosphor materials $P_R$, $P_G$, $P_B$. The phosphor materials respectively comprise (i) $P_R$ a europium (Eu) activated yttrium oxide $Y_{1.94}Eu_{0.06}O_3$ which generates red light of wavelength $\lambda_R$=612 nm, (ii) $P_G$ a europium/manganese (Mn) activated barium magnesium aluminate $Ba_{0.9}Eu_{0.1}Mg_{0.6}Mn_{0.4}Al_{10}O_7$ which generates green light of wavelength $\lambda_G$=514 nm and (iii) $P_B$ a europium activated barium magnesium aluminate $Ba_{0.9}Eu_{0.1}MgAl_{10}O_{17}$ which generates blue light of wavelength $\lambda_B$=444 to 445 nm. The four phosphor blends respectively comprise weight ratio blends of the phosphors $P_R$, $P_G$, $P_B$ of: blend 1—4/1/1, blend 2—8/1/1, blend 3—8/2/1 and blend 4—16/2/1. The photo-luminescent security marking was excited by excitation radiation of wavelength $\lambda_{ex}$=400 nm generated by an indium gallium nitride (InGaN) based LED. The emission spectra have been normalized to the second emission peak corresponding to light generated by the green phosphor $P_G$ ($Ba_{0.9}Eu_{0.1}Mg_{0.6}Mn_{0.4}Al_{10}O_7$). FIG. 7(b) is a portion of spectra at longer wavelengths showing the third emission peak in greater detail. Table 1 tabulates respective values for the normalized intensities $I_B$, $I_G$, $I_R$ of the emission peaks and the normalized intensity $I_{R/G}$ of the trough between the first and second emission peaks together with ratios of the emission peaks and emission peaks to the emission trough.

TABLE 1

Normalized peak intensity and ratio of normalized peak intensities for different weight ratio blends of three phosphors $P_R$, $P_G$ and $P_B$.

| Phosphor blend | | Normalized intensity (a · u) | | | | Ratio of normalized intensities | | | | | |
|---|---|---|---|---|---|---|---|---|---|---|---|
| | weight ratio | Peaks | | | trough | | | | | | |
| No. | $P_R/P_G/P_B$ | $I_R$ | $I_G$ | $I_B$ | $I_{R/G}$ | $I_B:I_G$ | $I_R:I_G$ | $I_B:I_R$ | $I_R:I_{R/G}$ | $I_{R/G}:I_G$ | $I_B:I_{R/G}$ |
| 1 | 4/1/1 | 0.17 | 1.00 | 1.50 | 0.15 | 1.50 | 0.17 | 8.82 | 1.13 | 0.15 | 10.00 |
| 2 | 8/1/1 | 0.31 | 1.00 | 1.25 | 0.13 | 1.25 | 0.31 | 4.03 | 2.38 | 0.13 | 9.61 |
| 3 | 8/2/1 | 0.21 | 1.00 | 0.78 | 0.11 | 0.78 | 0.21 | 3.71 | 1.91 | 0.11 | 7.09 |
| 4 | 16/2/1 | 0.30 | 1.00 | 0.77 | 0.11 | 0.77 | 0.30 | 2.57 | 2.73 | 0.11 | 7.00 |

It will be apparent from Table 1 that each phosphor blend has a characteristic set of parameters (i.e. ratio of normalized intensities). FIG. 7 illustrates how different weight ratio blends of the phosphor materials produce a respective emission spectrum in which the wavelengths of the peaks and/or troughs are substantially unchanged but which have a characteristic ratio of emission peak intensities and/or ratio of emission peak to trough intensities. A particular benefit of using different weight ratio blends of the same phosphor materials is that since each will produce peaks and/or trough at the substantially the same wavelength a simple optical detector arrangement that measures intensity for selected wavelength ranges, such as those illustrated in FIGS. 2, 3 and 4, can be utilized.

The authentication system of the invention is particularly suited for use with inorganic phosphors such as for example silicate-based phosphor of a general composition $A_3Si(O,D)_5$ or $A_2Si(O,D)_4$ in which Si is silicon, O is oxygen, A comprises strontium (Sr), barium (Ba), magnesium (Mg) or calcium (Ca) and D comprises chlorine (Cl), fluorine (F), nitrogen (N) or sulfur (S). Examples of silicate-based phosphors are disclosed in our co-pending patent applications US2006/0145123, US2006/0261309, US2007/0029526 and U.S. Pat. No. 7,311,858 (also assigned to Intematix Corporation) the content of each of which is hereby incorporated by way of reference thereto.

As taught in US2006/0145123, a europium ($Eu^{2+}$) activated silicate-based green phosphor has the general formula $(Sr,A_1)_x(Si,A_2)(O,A_3)_{2+x}:Eu^{2+}$ in which: $A_1$ is at least one of a $2^+$ cation, a combination of $1^+$ and $3^+$ cations such as for example Mg, Ca, Ba, zinc (Zn), sodium (Na), lithium (Li), bismuth (Bi), yttrium (Y) or cerium (Ce); $A_2$ is a $3^-$, $4^+$ or $5^+$ cation such as for example boron (B), aluminum (Al), gallium (Ga), carbon (C), germanium (Ge), N or phosphorus (P); and $A_3$ is a $1^-$, $2^-$ or $3^-$ anion such as for example F, Cl, bromine (Br), N or S. The formula is written to indicate that the $A_1$ cation replaces Sr; the $A_2$ cation replaces Si and the $A_3$ anion replaces oxygen. The value of x is an integer or non-integer between 1.5 and 2.5.

U.S. Pat. No. 7,311,858 discloses a silicate-based yellow-green phosphor having a formula $A_2SiO_4$:$Eu^{2+}$ D, where A is at least one of a divalent metal comprising Sr, Ca, Ba, Mg, Zn or cadmium (Cd); and D is a dopant comprising F, Cl, Br, iodine (I), P, S and N. The dopant D can be present in the phosphor in an amount ranging from about 0.01 to 20 mole percent and at least some of the dopant substitutes for oxygen anions to become incorporated into the crystal lattice of the phosphor. The phosphor can comprise $(Sr_{1-x-y}Ba_xM_y)SiO_4$:$Eu^{2+}$D in which M comprises Ca, Mg, Zn or Cd and where $0 \le x \le 1$ and $0 \le y \le 1$.

US2006/0261309 teaches a two phase silicate-based phosphor having a first phase with a crystal structure substantially the same as that of $(M1)_2SiO_4$; and a second phase with a crystal structure substantially the same as that of $(M2)_3SiO_5$ in which M1 and M2 each comprise Sr, Ba, Mg, Ca or Zn. At least one phase is activated with divalent europium ($Eu^{2+}$) and at least one of the phases contains a dopant D comprising F, Cl, Br, S or N. It is believed that at least some of the dopant atoms are located on oxygen atom lattice sites of the host silicate crystal.

US2007/0029526 discloses a silicate-based orange phosphor having the formula $(Sr_{1-x}M_x)_yEu_zSiO_5$ in which M is at least one of a divalent metal comprising Ba, Mg, Ca or Zn; $0<x<0.5$; $2.6<y<3.3$; and $0.001<z<0.5$. The phosphor is configured to emit visible light having a peak emission wavelength greater than about 565 nm.

The phosphor can also comprise an aluminate-based material such as is taught in our co-pending patent application US2006/0158090 and U.S. Pat. No. 7,390,437 (also assigned to Intematix Corporation) or an aluminum-silicate phosphor as taught in co-pending application US2008/0111472 the content of each of which is hereby incorporated by way of reference thereto.

US2006/0158090 teaches an aluminate-based green phosphor of formula $M_{1-x}Eu_xAl_yO_{[1+3y/2]}$ in which M is at least one of a divalent metal comprising Ba, Sr, Ca, Mg, Mn, Zn, Cu, Cd, Sm or thulium (Tm) and in which $0.1<x<0.9$ and $0.5 \le y \le 12$.

U.S. Pat. No. 7,390,437 discloses an aluminate-based blue phosphor having the formula $(M_{1-x}Eu_x)_{2-z}Mg_zAl_yO_{[2+3y/2]}$ in which M is at least one of a divalent metal of Ba or Sr. In one composition the phosphor is configured to absorb radiation in a wavelength ranging from about 280 nm to 420 nm, and to emit visible light having a wavelength ranging from about 420 nm to 560 nm and $0.05<x<0.5$ or $0.2<x<0.5$; $3 \le y \le 12$ and $0.8 \le z \le 1.2$. The phosphor can be further doped with a halogen dopant H such as Cl, Br or I and be of general composition $(M_{1-x}Eu_x)_{2-z}Mg_zAl_yO_{[2+3y/2]}$:H.

US2008/0111472 teaches an aluminum-silicate orange-red phosphor with mixed divalent and trivalent cations of general formula $(Sr_{1-x-y}M_xT_y)_{3-m}Eu_m(Si_{1-z}Al_z)O_5$ in at least one divalent metal selected from Ba, Mg or Ca in an amount ranging from $0 \le x \le 0.4$; T is a trivalent metal selected from Y, lanthanum (La), Ce, praseodymium (Pr), neodymium (Nd), promethium (Pm), samarium (Sm), gadolinium (Gd), terbium (Tb), dysprosium (Dy), holmium (Ho), Erbium (Er), Tm, ytterbium (Yt), lutetium (Lu), thorium (Th), protactinium (Pa) or uranium (U) in an amount ranging from $0 \le y \le 0.4$ and z and m are in a range $0 \le z \le 0.2$ and $0.001 \le m \le 0.5$. The phosphor is configured such that the halogen resides on oxygen lattice sites within the silicate crystal.

The phosphor can also comprise a nitride-based red phosphor material such as is taught in our co-pending provisional patent application 61/054,399 the content of which is hereby incorporated by way of reference thereto. 61/054,399 teaches a nitride-based red phosphor having the formula $M_mM_aM_bD_{3w}N_{[(2/3)m+z+a+(4/3)b-w]}Z_x$ where $M_m$ is a divalent element selected from beryllium (Be), Mg, Ca, Sr, Ba, Zn, Cd or mercury (Hg); $M_a$ is a trivalent element selected from B, Al, Ga, In, Y, Se, P, As, La, Sm, antimony (Sb) or Bi; $M_b$ is a tetravalent element selected from C, Si, Ge, tin (Sn), Ni, hafnium (Hf), molybdenum (Mo), tungsten (W), Cr, Pb, Ti or zirconium (Zr); D is a halogen selected from F, Cl, Br or I; Z is an activator selected from Eu, Ce, Mn, Tb or Sm, and N is nitrogen in amounts $0.01 \le m \le 1.5$, $0.01 \le a \le 1.5$, $0.01 \le b \le 1.5$, $0.0001 \le w \le 0.6$ and $0.0001 \le z \le 0.5$. The phosphor is configured to emit visible light with an emission peak wavelength greater than 640 nm.

It will be appreciated that the phosphor is not limited to the examples described herein and can comprise any phosphor material including both up-converting or down-converting phosphors that are organic or inorganic phosphor materials such as for example nitride and/or sulfate phosphor materials, oxy-nitrides and oxy-sulfate phosphors or garnet materials (YAG).

It is contemplated, in other embodiments, to use two or more individually operable excitation sources (LEDs) 26 to excite the photo-luminescent security marking with different wavelength excitation radiation and to measure the emission spectra and/or selected parameter(s) of the emission spectra for the various combinations of operation of the excitation sources. Operating the excitation sources in different combinations/permutations and measuring the emission spectrum and/or selected parameter(s) provides a further level of security for verifying the authenticity of the photo-luminescent security marking. In such an arrangement each source 26 when operated generates excitation radiation with a respective wavelengths $\lambda_{ex1}$ $\lambda_{ex2}$ and can comprise, for example, LEDs that emit excitation radiation of 400 nm and 465 nm. Examples of LEDs and their emission wavelengths are given in Table 2.

TABLE 2

Light emitting diodes (LEDs) and emission wavelengths $\lambda_e$.

| Color | LED | Emission wavelength $\lambda_e$ |
|---|---|---|
| Red | Aluminum gallium arsenide (AlGaAs) | 610 nm < $\lambda_e$ < 760 nm |
|  | Gallium arsenide phosphide (GaAsP) |  |
|  | Aluminum gallium indium phosphide (AlGaInP) |  |
| Orange | Gallium arsenide phosphide (GaAsP) | 590 nm < $\lambda_e$ < 610 nm |
|  | Aluminum gallium indium phosphide (AlGaInP) |  |
| Yellow | Gallium arsenide phosphide (GaAsP) | 570 nm < $\lambda_e$ < 590 nm |
|  | Aluminum gallium indium phosphide (AlGaInP) |  |
| Green | Gallium(III) nitride (GaN) | 500 nm < $\lambda_e$ < 570 nm |
|  | Gallium(III) phosphide (GaP) |  |
|  | Aluminum gallium indium phosphide (AlGaInP) |  |
|  | Aluminum gallium phosphide (AlGaP) |  |
| Blue | Zinc selenide (ZnSe) | 450 nm < $\lambda_e$ < 500 nm |
|  | Indium gallium nitride (InGaN) |  |
| Violet | Indium gallium nitride (InGaN) | 400 < $\lambda_e$ < 450 nm |
| Ultra violet | Aluminum nitride (AlN) | $\lambda_e$ < 400 nm |
|  | Aluminum gallium nitride (AlGaN) |  |

In such a system the photo-luminescent security marking comprises a blend of (i) at least one phosphor material that is only excitable by excitation radiation of a first wavelength $\lambda_{ex1}$ (e.g. 400 nm) and (ii) at least one phosphor material that is excitable by radiation of both excitation wavelengths $\lambda_{ex1}$ and $\lambda_{ex2}$ (e.g. excitation radiation within a wavelength range 400 to 465 nm). In other words one phosphor material is only excitable by excitation radiation of a first wavelength range and one phosphor material is excitable by excitation radiation of a second wavelength range which overlaps and includes the first wavelength range. Each phosphor material when excited emits light with a respective emission peak (P1, P2) at a respective different wavelength. Examples of suitable phosphor materials are given in Tables 3 and 4.

TABLE 3

Examples of phosphors that are excitable by excitation radiation of a first wavelength $\lambda_{ex1}$ (e.g. 400 nm).

| Phosphor composition | Excitation range | Emission peak P1 |
|---|---|---|
| Eu activated yttrium oxide: $Y_{2-x}Eu_xO_3$ where $0.01 \leq x \leq 0.2$ | ≈140-400 nm | ≈610-612 |
| Eu/Mn activated barium magnesium aluminate: $Ba_{1-x}Eu_xMg_{1-y}Mn_yAl_{10}O_7$ where $0.01 \leq x \leq 0.2$ and $0.01 \leq y \leq 0.9$ | ≈140-460 nm | ≈514-518 nm |
| Eu activated barium magnesium aluminate: $Ba_{1-x}Eu_xMgAl_{10}O_{17}$ where $0.01 \leq x \leq 0.2$ | ≈140-460 nm | ≈445-455 nm |

TABLE 4

Examples of phosphors that are excitable by both excitation radiation of a first wavelength $\lambda_{ex1}$ (e.g. 400 nm) and second wavelength $\lambda_{ex2}$ (e.g. 465 nm).

| Phosphor composition | Excitation range | Emission peak P2 |
|---|---|---|
| Eu activated Silicate (green/yellow): $(Sr_{1-x}Ba_x)_2SiO_4$:Eu $0 \leq x \leq 1$ | ≈200-490 nm | ≈507-575 nm |

Figure 8A:
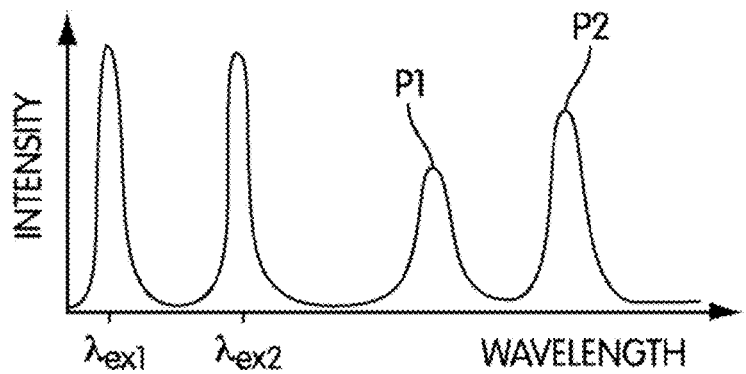
FIG. 8 shows schematic emission spectra (intensity versus wavelength) for a photo-luminescent security marking excited by excitation radiation (a) of first and second wavelengths (b) of a first wavelength only and (c) of a second wavelength only.
Figure 8B:
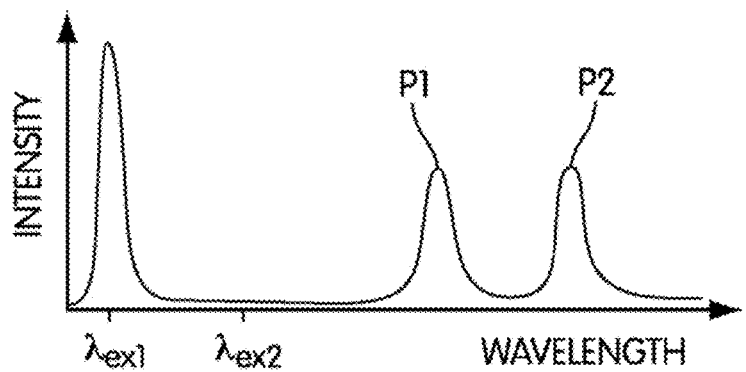
Figure 8C:
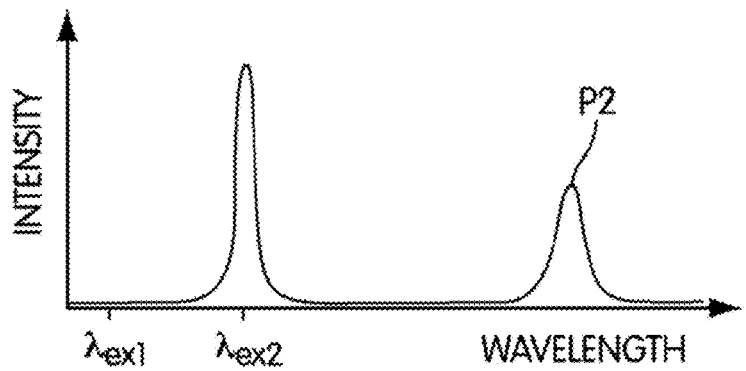

Operation of such an authentication system will now be described with reference to FIG. 8 which shows schematic emission spectra for a photo-luminescent security marking excited by excitation radiation (a) of the first and second wavelengths $\lambda_{ex1}$ and $\lambda_{ex2}$ (b) of the first wavelength $\lambda_{ex1}$ only and (c) of the second wavelength $\lambda_{ex2}$ only. In operation when both excitation sources are activated and the photo-luminescent security marking is irradiated with excitation radiation of both wavelengths $\lambda_{ex1}$ and $\lambda_{ex2}$, the emission spectrum (as shown in FIG. 8(a)) will be the sum of emissions from the two phosphor materials in which there will be a proportionally larger contribution from the second phosphor material since this is excitable by excitation radiation of both wavelengths. When the photo-luminescent security marking is irradiated with excitation radiation of the first wavelength only, the emission spectrum (as shown in FIG. 8(b)) will again be the sum of emissions from the first and second phosphor materials but with a relatively weaker contribution from the second phosphor material. Finally when the photo-luminescent security marking is irradiated with excitation radiation of the second wavelength only, the emission spectrum (as shown in FIG. 8(c)) will contain only a contribution from the second phosphor material. Thus by operating the excitation sources in different combinations/permutations and measuring the emission spectrum and/or selected parameter(s) of the emission spectrum, such for example the ratio of the intensities of the first and second emission peaks, this provides a further level of security for verifying the authenticity of the photo-luminescent security marking. The different combinations of "on" and "off" for the two excitation sources can be programmed into the microprocessor.

In yet a further embodiment it is contemplated to use three individually operable excitation sources to excite the photo-luminescent security marking and to measure the emission spectrum and/or selected parameters of the emission spectrum for various combinations of actuated sources. For example each excitation source can comprise an LED which is operable to generate excitation radiation of a respective excitation wavelength $\lambda_{ex1}$, $\lambda_{ex2}$ and $\lambda_{ex3}$ (e.g. 400 nm, 465 nm and 525 nm). In such an arrangement the photo-luminescent security marking comprises a blend of (i) at least one phosphor material that is only excitable by radiation of the first wavelength $\lambda_{ex1}$ (e.g. 400 nm), (ii) at least one phosphor material that is excitable by radiation of both the first $\lambda_{ex1}$ and $\lambda_{ex2}$ second wavelengths (e.g. excitation radiation with a wavelength range 400 to 460 nm), and (iii) at least one phosphor material that is excitable by radiation of all excitation wavelengths $\lambda_{ex1}$, $\lambda_{ex2}$ and $\lambda_{ex3}$ (e.g. excitation radiation with a wavelength range 400 to 510 nm). In general the phosphor materials each have an emission peak at a respective different wavelength.

TABLE 5

Examples of phosphors that are excitable by excitation radiation of a first wavelength $\lambda_{ex1}$ (e.g. 400 nm), second wavelength $\lambda_{ex2}$ (e.g. 465 nm) and third wavelength $\lambda_{ex3}$ (e.g. 520 nm).

| Phosphor composition | Excitation range | Emission peak P3 |
|---|---|---|
| Eu activated Silicate (orange): $(Sr_{1-x}Ba_x)_3SiO_5$:Eu $0 \leq x \leq 1$ | ≈200-560 nm | ≈586-600 nm |
| Eu activated aluminum silicate (orange): $(Y_ySr_{1-x-y}Ba_x)_3(Al_zSi_{1-z})O_5$:Eu $0 \leq x \leq 0.4, 0 \leq y \leq 0.4$ and $0 \leq z \leq 0.2$ | ≈200-580 nm | ≈600-620 nm |
| Eu activated nitride (red): $CaAlSiN_3$:Eu | ≈250-600 nm | ≈550-800 nm |
| Eu activated nitride (red): | | |
| $Ca_2Si_5N_8$:Eu | ≈250-550 nm | ≈500-800 nm |
| $Sr_2Si_5N_8$:Eu | ≈200-600 nm | ≈550-850 nm |
| $Ba_2Si_5N_8$:Eu | ≈250-550 nm | ≈500-850 nm |

With three excitation sources there are seven different combinations in which the excitation sources can be operated these being:
excitation source one only ($\lambda_{ex1}$),
excitation source two only ($\lambda_{ex2}$),
excitation source three only ($\lambda_{ex3}$),
excitation sources one and two ($\lambda_{ex1}+\lambda_{ex2}$),
excitation sources one and three ($\lambda_{ex1}+\lambda_{ex3}$),
excitation sources two and three ($\lambda_{ex2}+\lambda_{ex3}$) and
all three excitation sources ($\lambda_{ex1}+\lambda_{ex2}+\lambda_{ex3}$).

In operation when all three excitation sources are operable and the photo-luminescent security marking is irradiated with excitation radiation of all three wavelengths $\lambda_{ex1}$, $\lambda_{ex2}$, $\lambda_{ex3}$, the emission spectrum will be the sum of emissions from the three phosphor materials in which there will be a proportionally larger contribution from the second and third phosphor materials since each of these is excitable by excitation radiation of at least two wavelengths ($\lambda_{ex1}$ and $\lambda_{ex2}$). When only the first excitation source is operated, the photo-luminescent security marking is irradiated with excitation radiation of the first wavelength $\lambda_{ex1}$ only and the emission spectrum will again be the sum of emissions from the three phosphor materials but with a relatively weaker contribution from the second and third phosphor materials. When only the second excitation source is operated, the photo-luminescent security marking is irradiated with excitation radiation of the second wavelength $\lambda_{ex2}$ only and the emission spectrum will be the sum of emissions from the second and third phosphor material only. When only the third excitation source is operated, the photo-luminescent security marking is irradiated with excitation radiation of the third wavelength $\lambda_{ex3}$ only and the emission spectrum will correspond to emission from the third phosphor material only. When the first and second excitation sources are operable, the photo-luminescent security marking is irradiated with excitation radiation of wavelengths $\lambda_{ex1}, \lambda_{ex2}$, and the emission spectrum will be the sum of emissions from the three phosphor materials in which the contribution from the third phosphor material with be lower than the situation when all three sources are operable. When the first and third excitation sources are operable, the photo-luminescent security marking is irradiated with excitation radiation of wavelengths $\lambda_{ex1}, \lambda_{ex3}$, and the emission spectrum will be the sum of emissions from the three phosphor materials in which the contribution from the third phosphor material will be higher than the situation in which the first and second are operable. Finally, when the second and third excitation sources are operable, the photo-luminescent security marking is irradiated with excitation radiation of wavelengths $\lambda_{ex2}, \lambda_{ex3}$, and the emission spectrum will be the sum of emissions from the second and third phosphor materials in which the magnitude of each contribution is lower since the second phosphor is excited by radiation of a single wavelength and the third phosphor is excited by radiation of two wavelengths. As a result the photo-luminescent marking can produce up to seven different emission spectra depending on which excitation sources are operable.

Figure 9A:
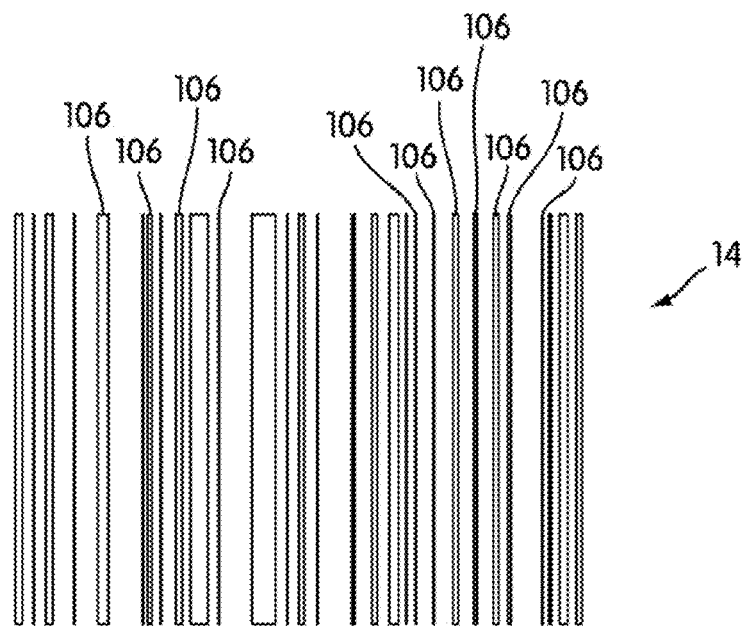
FIGS. 9(a) and 9(b) show schematic representations of a photo-luminescent marking in the form of bar codes.
Figure 9B:
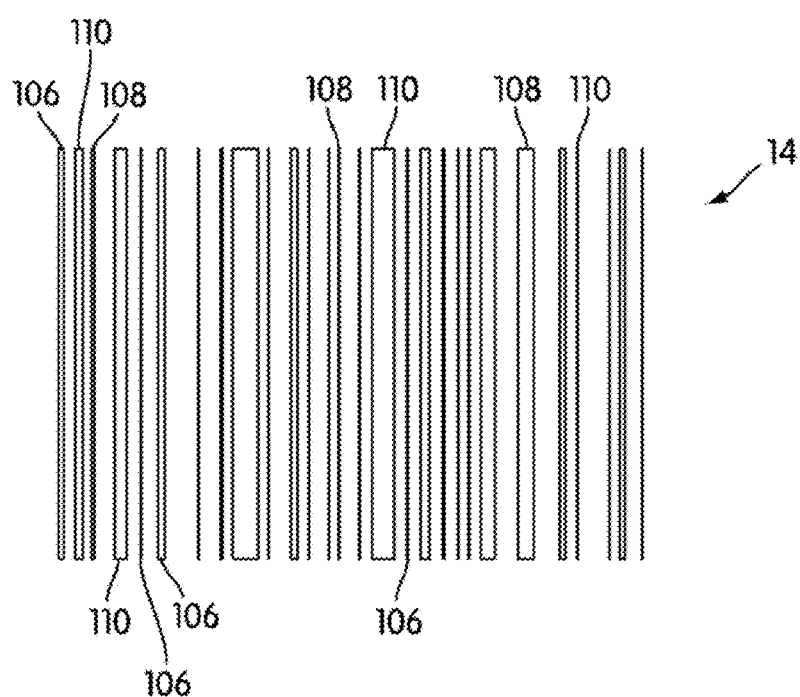

It will be appreciated that the present invention is not restricted to the specific embodiments described and that variations can be made that are within the scope of the invention. For example, in other embodiments it is contemplated that the photo-luminescent security marking 14 incorporates a further security device such as for example a bar code. Photo-luminescent security markings in the form of a bar code are shown in FIGS. 9(a) and 9(b). As is known a bar code comprises a series of parallel lines (bars) whose width and/or spacing is used to encode data. As shown in FIG. 9(a), and in accordance with the invention, a photo-luminescent bar code marking comprises a series of parallel lines 106 that are composed of an ink containing a blend of at least two phosphor materials. The photo-luminescent bar code marking 14 can be read using a conventional bar code scanner arrangement that uses light that does not excite the phosphor materials and the phosphor marking verified using the authentication device described above. In other arrangements as illustrated in FIG. 9(b) the bar code can comprise a series of bars 106, 108, 110 containing different phosphors and/or phosphor blends. With such a photo-luminescent security marking the authentication device preferably scans the bar code with excitation radiation and the emission spectrum is measured for individual bars and/or selected groups of bars. The bars 106, 108, 110 containing different phosphor materials can be arranged in a set sequence or their sequence encoded by for example linking their sequence to the bar coding. In one arrangement bars of a specific width can comprise a respective phosphor or phosphor blend. In other arrangements the photo-luminescent marking can be provided in the spaces between lines of the bar code. It will be appreciated that the photo-luminescent marking of the invention can be incorporated into other forms of coding such as a matrix code, essentially a 2-dimensional bar code, in which data is encoded in the form of a pattern of dots, squares and other geometric symbols.

What is claimed is:

1. A method of authenticating a photo-luminescent security marking in which an authentic security marking comprises a blend of at least two phosphor materials, the method comprising:
   a) irradiating the marking with a first excitation radiation of only a first wavelength within a first wavelength range, wherein the first radiation having only the first wavelength excites both a first phosphor and a second phosphor, and measuring at least one selected parameter of light emitted by the first phosphor and the second phosphor within the marking,
   b) irradiating the marking with a second excitation radiation of only a second wavelength that is within a second wavelength range, wherein the second radiation having only the second wavelength excites only the second phosphor, and measuring the at least one selected parameter of light emitted by the second phosphor within the marking,
   c) irradiating the marking with a third excitation radiation that includes both the first and second wavelengths, wherein the third radiation having the first and second wavelengths excites both the first phosphor and the second phosphor, and measuring the at least one selected parameter of light emitted by the first phosphor and the second phosphor within the marking, and
   d) comparing the selected parameters measured in a), b) and c) with corresponding parameters of the known emission characteristic and if the parameters are within prescribed limits verifying the authenticity of the marking.

2. The method according to claim 1, wherein the at least one selected parameter comprises intensity of selected wavelength region.

3. The method according to claim 1, wherein the at least one selected parameter comprises ratio of intensities of selected wavelength regions.

4. The method according to claim 1, wherein the at least one selected parameter comprises intensity of an emission peak.

5. The method according to claim 1, wherein the at least one selected parameter comprises wavelength of an emission peak.

6. The method according to claim 1, wherein the at least one selected parameter comprises rate of rise of an emission peak.

7. The method according to claim 1, wherein the at least one selected parameter comprises rate of fall of an emission peak.

8. The method according to claim 1, wherein the at least one selected parameter comprises ratio of emission peak intensities.

9. The method according to claim 1, wherein the at least one selected parameter comprises ratio of emission peak wavelengths.

10. The method according to claim 1, wherein the at least one selected parameter comprises intensity of an emission trough.

11. The method according to claim 1, wherein the at least one selected parameter comprises wavelength of an emission trough.

12. The method according to claim 1, wherein the at least one selected parameter comprises ratio of emission trough intensities.

13. The method according to claim 1, wherein the at least one selected parameter comprises ratio of emission trough wavelengths.

14. The method according to claim 1, wherein the at least one selected parameter comprises wavelength of a point of inflection.

15. The method according to claim 1, wherein the at least one selected parameter comprises intensity of a point of inflection.

16. The method according to claim 1, wherein the at least one selected parameter comprises ratio of point of inflection intensities.

17. The method according to claim 1, wherein the at least one selected parameter comprises ratio of points of inflection wavelengths.

18. The method according to claim 1, wherein the at least one selected parameter comprises number of emission peaks.

19. The method according to claim 1, wherein the at least one selected parameter comprises number of emission troughs.

20. The method according to claim 1, wherein the at least one selected parameter comprises number of points of inflection.

21. The method according to claim 1, wherein the at least one selected parameter comprises shape of emission peak.

22. The method according to claim 1, wherein irradiating the marking with the third excitation radiation causes the at least one selected parameter of light that is measured to include a combination of emissions by the second phosphor corresponding to both the first wavelength and the second wavelength.

* * * * *